United States Patent
Orr et al.

(10) Patent No.: US 7,135,001 B2
(45) Date of Patent: Nov. 14, 2006

(54) REBREATHING METHODS INCLUDING OSCILLATING, SUBSTANTIALLY EQUAL REBREATHING AND NONREBREATHING PERIODS

(75) Inventors: Joseph A. Orr, Park City, UT (US); Kai Kuck, Salt Lake City, UT (US); Lara Brewer, Bountiful, UT (US)

(73) Assignee: RIC Investments, LLC, Wilmington, DE (US)

( * ) Notice: Subject to any disclaimer, the term of this patent is extended or adjusted under 35 U.S.C. 154(b) by 383 days.

(21) Appl. No.: 09/813,225

(22) Filed: Mar. 20, 2001

(65) Prior Publication Data

US 2002/0174866 A1 Nov. 28, 2002

(51) Int. Cl.
*A61B 5/02* (2006.01)
*A61B 5/08* (2006.01)

(52) U.S. Cl. .................. 600/526; 600/504; 600/529

(58) Field of Classification Search ............... 600/300, 600/481, 529–534, 526
See application file for complete search history.

(56) References Cited

U.S. PATENT DOCUMENTS

| | | |
|---|---|---|
| 4,221,224 A | 9/1980 | Clark |
| 4,363,327 A | 12/1982 | Clark |
| 4,463,764 A | 8/1984 | Anderson et al. |
| 4,608,995 A | 9/1986 | Linnarsson et al. |
| 5,060,656 A | 10/1991 | Howard |
| 5,069,220 A | 12/1991 | Casparie et al. |
| 5,117,674 A | 6/1992 | Howard |
| 5,178,155 A | 1/1993 | Mault |
| 5,285,794 A | 2/1994 | Lynch |
| 5,299,579 A | 4/1994 | Gedeon et al. |
| 5,402,796 A | 4/1995 | Packer et al. |
| 5,632,281 A | 5/1997 | Rayburn |
| 5,836,300 A | 11/1998 | Mault |
| 5,971,934 A | 10/1999 | Scherer et al. |
| 6,102,868 A | 8/2000 | Banner et al. |
| 6,106,480 A * | 8/2000 | Gama De Abreu et al. .................. 600/529 |
| 6,200,271 B1 * | 3/2001 | Kuck et al. .................. 600/532 |
| 6,210,342 B1 * | 4/2001 | Kuck et al. .................. 600/504 |
| 6,238,351 B1 * | 5/2001 | Orr et al. .................. 600/532 |
| 6,258,038 B1 * | 7/2001 | Haryadi et al. ............. 600/504 |
| 6,342,039 B1 * | 1/2002 | Lynn et al. .................. 600/529 |
| 6,413,226 B1 * | 7/2002 | Starr et al. .................. 600/532 |
| 6,517,496 B1 * | 2/2003 | Mault .................. 600/532 |

(Continued)

FOREIGN PATENT DOCUMENTS

DE 28 49 217 A1 5/1980

(Continued)

OTHER PUBLICATIONS

"Noninvasive cardiac output measurement in orthostasis: pulse contour analysis compared with acetylene rebreathing", Stok et al., J. Appl Physiol. 1999: Dec., 87(6): 2266-73.*

(Continued)

*Primary Examiner*—Charles A Marmor, II
*Assistant Examiner*—Patricia C. Mallari
(74) *Attorney, Agent, or Firm*—TraskBritt

(57) ABSTRACT

A differential Fick technique including a first phase in which baseline breathing parameters may be established and a second phase in which a change in the effective ventilation of a patient is induced. The durations of the first and second phases may be substantially the same and may be abbreviated relative to the durations of comparable phases of previously known differential Fick techniques. The disclosed differential Fick technique also lacks a recovery period in which the respiratory parameters of a patient are permitted to return to "normal" levels.

81 Claims, 7 Drawing Sheets

U.S. PATENT DOCUMENTS 6,540,689 B1 *   4/2003   Orr et al. .................... 600/529

FOREIGN PATENT DOCUMENTS

| WO | 96/24285 | 8/1996 |
|---|---|---|
| WO | WO 98/12963 | 4/1998 |
| WO | WO 98/26710 | 6/1998 |
| WO | WO 00/42908 | 7/2000 |
| WO | WO 00/67634 | 11/2000 |
| WO | WO 01/62148 | 8/2001 |

OTHER PUBLICATIONS

"air", Webster's Revised Unabridged Dictionary, 1998.*
"immediate", Webster's Revised Unabridged Dictionary, 1998.*
"air". The American Heritage® Concise Dictionary (1994). http://www.xreferplus.com/entry/689507.*
H. Blomquist et al., *A Non-Invasive Technique for Measurement of Lung Perfusion*, Intensive Care Medicine 1986; 12:172.
R.J. Bosman et al, *Non-Invasive Pulimonary Blood Flow Measurement by Means of $CO_2$ Analysis Of Expiratory Gases*, Intensive Care Medicine 1991, 17:98-102.
A. Gedeon, *Non-Invasive Pulmonary Blood Flow for Optimal Peep*, ICOR AB, Ulvsundavagen 178 B, S-161 30 Bromma, Sweden, pp. 49-58.
Capek, J.M., *Noninvasive Measurement of Cardiac Output Using Partial $CO_2$ Rebreathing* [Dissertation], Rensselaer Polytechnic Institute (1988) 28:351 p. (due to large number of pages, only table of contents and abstract have been copied).
Capek, J.M., et al., *Noninvasive Measurement of Cardiac Output Using Partial $CO_2$ Rebreathing*, IEEE Trans. Biomed. Eng. (1988) 35(9):653-61.
Davies, Gerald G., et al., *Continuous Fick cardiac output compared to thermodilution cardiac output*, Critical Care Medicine (1986) 14(10):881-85.
Elliot, C. Gregory, et al., *Complications of Pulmonary Artery Catheterization in the Care of Critically Ill Patients*, Chest (1979) 76:647-52.
Fick, A., *Über die Messung des Blutquantums in den Herzventrikeln*, Sitzungsbericht der Physikalisch-Medizinischen Gesellschaft zu Würzburg (1870) 36 (2 pages).
Gama de Abreu, Marcelo, et al., *Measurement of Pulmonary Capillary Blood Flow for Trending Mixed Venous Blood Oxygen Saturation and Oxygen Delivery*, Crit. Care Med. (1998), vol. 26, No. 1 (Suppl.), A106, Abstract #238, (1 page).
Gama de Abreu, Marcelo, et al., *Is the Partial $CO_2$ Rebreathing Technique a Useful Tool for Trending Pulmonary Capillary Blood Flow During Adjustments of Peep?*, Crit. Care Med. (1998), vol. 26, No. 1 (Suppl.), A106, Abstract #237, (1 page).
Gama de Abreu, et al., *Partial carbon dioxide rebreathing: A reliable technique for noninvasive measurement of nonshunted pulmonary capillary blood flow*, Crit. Care Med. (1997) 25(4):675-83.

Gedeon, A., et al., *Noninvasive Cardiac Output Determined with a New Method Based on Gas Exchange Measurements and Carbon Dioxide Rebreathing: A Study in Animals/Pigs*, J. Clin. Monit. (1992) 8(4):267-78
Gedeon, A., et al., *A new method for noninvasive bedside determination of pulmonary blood flow*, Med. & Biol. Eng. & Comput. (1980) 18:411-418.
Guyton, A.E., et al., *Measurement of cardiac output by the direct Fick method*, In: Cardiac output and its regulation, W.B. Saunders Company (1973) 21-39.
Kyoku, I., et al. *Measurement of cardiac output by Fick method using $CO_2$ analyzer Servo*, Kyobu Geka. Japanese Journal of Thoracic Surgery (1988) 41(12):966-70.
Lynch, J., et al., *Comparison of a modified Fick method with thermodilution for determining cardiac output in critically ill patients on mechanical ventilation*, Intensive Care Med. (1990) 16:248-51.
Mahutte, C. Kees, et al., *Relationship of Thermodilution Cardiac Output to Metabolic Measurements and Mixed Venous Oxygen Saturation*, Chest (1993) 104(4):1236-42.
Miller, D.M., et al., *A Simple Method for the Continuous Noninvasive Estimate of Cardiac Output Using the Maxima Breathing System. A Pilot Study*, Anaesth. Intens. Care (1997) 25(1):23-28.
Österlund, B., et al., *A new method of using gas exchange measurements for the noninvasive determination of cardiac output: clinical experiences in adults following cardiac surgery*, Acta Anaesthesiol Scand (1995) 39:727-32.
Sackner, Marvin A., *Measurement of cardiac output by alveolar gas exchange*, Handbook of Physiology–The Respiratory System IV, Chapter 13, 233-55.
Spalding, H. K., et al., *Carbon Dioxide ($CO_2$) Elimination Rate Accurately Predicts Cardiac Output*, Anesthesiology (1997) 87(3A) (1 page).
Sprung, Charles L., et al., *Ventricular Arrhythmias During Swan-Ganz Catheterization of the Critically Ill*, Chest (1981) 79:413-15.
Taskar, V., et al., *Dynamics of Carbon Dioxide Elimination Following Ventilator Resetting*, Chest (1995) 108:196-202.
Winkler, Tilo, et al., *Pulmonary Capillary Blood Flow by Partial $CO_2$ Rebreathing: A Simulation Study Using A Bicompartmental Model of Gas Exchange*, Crit. Care Med. (1998), vol. 26, No. 1 (Suppl.), A105, Abtract #234, (1 page).
Roy, Rob J., et al., *Noninvasive Differential Blood Flow Monitoring During One-Lung Anesthesia*, IEEE Engineering in Medicine & Biology Soc. 11th Annual Internat'l. Conference-1413 (1989) (2 pages).
Gama de Abreu, M., et al., *Reliability of the Partial $CO_2$ Rebreathing Technique for Measurement of Cardiac Output*, Proceedings RC IEEE-EMBS & 14th BMESI (1995), pp. 4.15-4.16.
Jaffe, Michael B., *Partial $CO_2$ Rebreathing Cardiac Output-Operating Principles of the NICO™ System*, Jour. of Clinical Monitoring & Computing (1999), vol. 15, pp. 387-401.
PCT International Search Report of Jul. 22, 2002.

* cited by examiner

REBREATHING METHODS INCLUDING OSCILLATING, SUBSTANTIALLY EQUAL REBREATHING AND NONREBREATHING PERIODS

BACKGROUND OF THE INVENTION

1. Field of the Invention

The present invention relates generally to methods for noninvasively determining the pulmonary capillary blood flow ("PCBF") or cardiac output ("CO") of a patient. Particularly, the present invention relates to so-called differential Fick techniques for determining PCBF or CO including partial rebreathing techniques.

2. Background of the Related Art

Pulmonary capillary blood flow and cardiac output are examples of various hemodynamic parameters that may be monitored in critically ill patients. Cardiac output is the sum of blood flow through the lungs that participates in gas exchange, which is typically referred to as pulmonary capillary blood flow, and the blood flow that does not participate in gas exchange, which is typically referred to as intrapulmonary shunt flow or venous admixture.

Conventionally, pulmonary capillary blood flow and cardiac output have been measured by direct, invasive techniques, such as by indicator dilution. Indicator dilution includes introducing a predetermined amount of an indicator into the bloodstream through the heart of a patient and analyzing blood downstream from the point of introduction to obtain a time vs. dilution curve. Thermodilution, in which room temperature or colder saline solution, which is also referred to as "cold" saline, is used as the indicator, is a widely employed type of indicator dilution. The cold saline is typically introduced into the right heart bloodstream of a patient through a Swan-Ganz catheter, which includes a thermistor at an end thereof. The thermistor is employed to measure the temperature of the blood after it has passed through the right heart, or downstream from the point at which the cold saline is introduced. A thermodilution curve is then generated from the data, from which the cardiac output of the patient may be derived. Thermodilution and other indicator dilution techniques are, however, somewhat undesirable due to the potential for harm to the patient that is associated with inserting and maintaining such catheters in place.

Less invasive indicator dilution methods that do not require that a catheter pass through the valves of the right side of the heart have also been developed. These less invasive methods include the so-called "transpulmonary indicator methods," which include the placement of probes in the esophagus or trachea (e.g., in Doppler/Transesophageal echocardiography). While the use of esophageal or endotracheal probes may seem less invasive than the introduction of a catheter into the heart of a patient, the potential for harming a patient exists nonetheless.

Thus, safer, noninvasive techniques for determining pulmonary capillary blood flow and cardiac output have been developed. These noninvasive techniques are typically based on some form of the basic physiological principle known as the Fick principle: the rate of uptake of a substance by the blood or release of a substance from blood at the lung is equal to the blood flow past the lung and the content difference of the substance at each side of the lung.

One variation of the Fick principle is the so-called carbon dioxide Fick equation:

$$Q_{pcbf} = V_{CO_2}/(CvCO_2 - CaCO_2), \quad (1)$$

where $Q_{pcbf}$ is pulmonary capillary blood flow, $V_{CO_2}$ is carbon dioxide elimination, $CvCO_2$ is carbon dioxide content of the venous blood of the patient, and $CaCO_2$ is the carbon dioxide content of the arterial blood of the patient.

Typically, a differential form of the carbon dioxide Fick equation is used to noninvasively determine the pulmonary capillary blood flow or cardiac output of a patient. Each of the differential Fick techniques for determining the pulmonary capillary blood flow or cardiac output of a patient are based on the fundamental premise that pulmonary capillary blood flow and cardiac output can be estimated based on the changes of other, measurable parameters when a change in the effective ventilation (i.e., the total ventilation less the wasted ventilation due to deadspace associated with the apparatus, the patient, or a combination thereof) occurs. When a differential form of the Fick equation is used, the pulmonary capillary blood flow or cardiac output of a patient may be determined on the basis of differences in $V_{CO_2}$, $CaCO_2$, and $CvCO_2$ between "normal" respiration and while a change in the effective ventilation of the patient is being induced. The following is an example of a differential Fick equation:

$$Q_{pcbfBD} = \frac{V_{CO_{2B}} - V_{CO_{2D}}}{(C_v CO_{2B} - C_v CO_{2D}) - (C_a CO_{2B} - C_a CO_{2D})}, \quad (2)$$

where $V_{CO_{2B}}$ and $V_{CO_{2D}}$ are, respectively, the carbon dioxide eliminations of the patient during "normal" breathing and while a change in the effective ventilation of the patient is being induced, $CvCO_{2B}$ and $CvCO_{2D}$ are the contents of carbon dioxide in the venous blood of the patient during the same periods, and $CaCO_{2B}$ and $CaCO_{2D}$ are the contents of carbon dioxide in the arterial blood of the patient during "normal" breathing and when the effective ventilation of the patient is changed, respectively.

Typically, differential Fick techniques rely upon baseline measurements (i.e., taken during "normal" respiration) of $V_{CO_2}$ and $PetCO_2$. Once baseline data has been gathered, a change in the effective ventilation of the patient is induced. Once the $V_{CO_2}$ and $PetCO_2$ values become stable with the change in effective ventilation, these parameters are again measured. The difference between the baseline values and those taken during the change in the effective ventilation of the patient are used to calculate the pulmonary capillary blood flow or cardiac output of the patient. When continually monitoring and updating the pulmonary capillary blood flow or cardiac output of a patient, a recovery period typically precedes reestablishment of the baseline values. The recovery period has been provided to facilitate the reestablishment of baseline levels prior to the start of rebreathing. Most investigators do not collect any data for analysis during the recovery period.

The carbon dioxide Fick equation (1) and the differential Fick carbon dioxide equation (2) each require a determination of the $V_{CO_2}$ of a patient. Carbon dioxide elimination is the net volume of carbon dioxide produced by the patient, or excreted from the body of a patient, during respiration. Therefore, carbon dioxide elimination is useful as an indicator of the metabolic rate of the patient. The $V_{CO_2}$ of a patient may be noninvasively measured as the difference, per breath, between the volume of carbon dioxide inhaled during inspiration and the volume of carbon dioxide exhaled during expiration. Carbon dioxide elimination over a breath is typically calculated as follows:

$$V_{CO_2} = \int_{breath} V \times f_{CO_2} dt, \quad (3)$$

where V is the measured respiratory flow and $f_{CO2}$ is the substantially simultaneously detected carbon dioxide signal, or fraction of the respiratory gases that comprises carbon dioxide, or "carbon dioxide fraction."

During rebreathing, the exhaled volume of carbon dioxide may change only slightly, while the inhaled volume of carbon dioxide, which is normally negligible, may increase substantially. As a consequence, the difference between the amounts of carbon dioxide that are exhaled and inhaled during rebreathing is reduced substantially, as is the carbon dioxide elimination of a patient.

A determination of the $CaCO_2$ of a patient is typically based upon the measured $PetCO_2$ of the patient. The $PetCO_2$, after correcting for any deadspace in the patient's airway or in a ventilation circuit, is typically assumed to be approximately equal to the partial pressure of carbon dioxide in the alveoli ($P_ACO_2$) of the patient's lungs or, if there is no intrapulmonary shunt, the partial pressure of carbon dioxide in the arterial blood of the patient ($PaCO_2$). Using a standard carbon dioxide dissociation curve, either the $PetCO_2$ measurement or the $PaCO_2$ calculation may be used to determine $CaCO_2$.

When a change in the effective ventilation of a patient occurs, such as when a patient inhales increased concentrations of carbon dioxide, $CaCO_2$ changes relatively quickly compared to the rate of change in $CvCO_2$, which has a higher carbon dioxide content $CaCO_2$. The content of carbon dioxide in the venous blood also changes relatively slowly because the body stores a large volume of carbon dioxide in other tissues. The carbon dioxide stores of an "average" human male may be as high as about 15 to 40 liters. Thus, the duration or magnitude of a change in the effective ventilation of a patient must be significant (e.g., the patient must inhale a significant amount of carbon dioxide) to effect a measurable change (e.g., increase) in the content of carbon dioxide in the patient's venous blood. Likewise, the $V_{CO2}$ of a patient changes at a faster rate than $CvCO_2$. In fact, $CvCO_2$ changes so slowly relative to the rates at which $CaCO_2$ and the $V_{CO2}$ change that, when a change in effective ventilation occurs over a relatively brief period of time (e.g., a few minutes or less), the $CvCO_2$ can be assumed to remain substantially the same (i.e., little or no change) over the time it takes to complete a conventional rebreathing maneuver. As the effects of rebreathing are delayed due to transport time and damping, conventional rebreathing processes typically employ a recovery period.

Carbon dioxide elimination and the $PetCO_2$ are typically measured during both of the phases of a differential Fick technique.

In one example of a known differential Fick technique for inducing a change in the effective ventilation of a patient, carbon dioxide may be added to the gases that are inhaled by the patient, either directly (e.g., by the addition of carbon dioxide from a cylinder or other external source) or by causing a patient to rebreathe previously exhaled gases. An exemplary differential Fick technique that has been employed, which is disclosed in Gedeon, A. et al. in 18 *Med. & Biol. Eng. & Comput.,* 411–418 (1980) (hereinafter "Gedeon"), employs a period of increased ventilation followed immediately by a period of decreased ventilation. When the technique disclosed in Gedeon or another so-called "rebreathing" process is used, the $V_{CO2}$ of the patient decreases to a level that is less than that which is measured during normal breathing. Rebreathing during which the $V_{CO2}$ decreases to near zero is typically referred to as "total rebreathing." Rebreathing that causes some decrease, but not a total reduction of $V_{CO2}$, is typically referred to as "partial rebreathing." These rebreathing processes may be used either to noninvasively estimate the $CvCO_2$, as in "total rebreathing," or to obviate the need to know $CvCO_2$, as in "partial rebreathing."

Rebreathing is typically conducted with a rebreathing circuit, which causes a patient to inhale a gas mixture that includes carbon dioxide. For example, the rebreathed air, which may be inhaled from a deadspace during rebreathing, includes air that has been exhaled by the patient (i.e., carbon dioxide-rich air).

During total rebreathing, substantially all of the gas inhaled by the patient was expired during the previous breath. Thus, during total rebreathing, $PetCO_2$ is typically assumed to be equal or closely related to the partial pressure of carbon dioxide in the arterial ($PaCO_2$), venous ($PvCO_2$), and alveolar ($P_ACO_2$) blood of the patient. Total rebreathing processes are based on the assumption that neither the pulmonary capillary blood flow or cardiac output, nor the $CvCO_2$ of the patient, changes substantially during the rebreathing process. The partial pressure of carbon dioxide in blood may be converted to the content of carbon dioxide in blood by means of a carbon dioxide dissociation curve, where the change in the carbon dioxide content of the blood ($CvCO_2$—$CaCO_2$) is equal to the slope(s) of the carbon dioxide dissociation curve multiplied by the measured change in $PetCO_2$, as caused by a change in effective ventilation, such as rebreathing.

In partial rebreathing, the patient inhales a mixture of "fresh" gases and gases that were exhaled during the previous breath. Thus, the patient does not inhale a volume of carbon dioxide as large as the volume of carbon dioxide that would be inhaled during a total rebreathing process.

As an example of a known partial rebreathing process, the NICO™ system offered by Novametrix Medical Systems Inc. of Wallingford, Conn., employs a 60 second baseline period, a 50 second rebreathing period, and a 70 second recovery period. The complete rebreathing cycle lasts for about three minutes. Another exemplary partial rebreathing process is disclosed in Capek, J M, and Roy, R J, Noninvasive measurement of cardiac output using partial $CO_2$ rebreathing, IEEE Trans. Biomed. Eng. 1988; 35:653–661. That rebreathing process has a total cycle time of about 3½ minutes, with the actual rebreathing phase lasting for about 30 seconds. Gama de Abreu, M, et al., Partial carbon dioxide rebreathing: A reliable technique for noninvasive measurement of nonshunted pulmonary capillary blood flow, Crit. Care Med. 1997; 25: 675–683, discloses a rebreathing process with a 35 second rebreathing phase and a total cycle time, including baseline and recovery phases, of about 3 minutes.

Conventional partial rebreathing processes typically employ a differential form of the carbon dioxide Fick equation, such as equation (2), to determine the pulmonary capillary blood flow or cardiac output of the patient without requiring knowledge of the carbon dioxide content of the venous blood of the patient since the carbon dioxide content of the venous blood of the patient is assumed to remain substantially the same (i.e., constant) in the periods during which measurements are obtained.

Again, with a carbon dioxide dissociation curve, the measured partial pressure of end tidal carbon dioxide can be used to determine the change in content of carbon dioxide in the blood before and during the rebreathing process. Accordingly, the following equation can be used to determine pulmonary capillary blood flow or cardiac output when partial rebreathing is conducted:

$$Q = \Delta V_{CO_2}/s\Delta PetCO_2, \tag{4}$$

where s is the slope of the carbon dioxide dissociation curve.

While partial rebreathing is the most commonly used method for causing a change in the effective ventilation of a patient, alternative differential Fick techniques for measuring pulmonary capillary blood flow or cardiac output have also been employed. Such differential Fick methods typically include a brief change of $PetCO_2$ and $V_{CO_2}$ in response to a change in effective ventilation. This brief change can be accomplished by adjusting the respiratory rate, inspiratory and/or expiratory times, tidal volume, inspiratory pause, or positive-end expiratory pressure (PEEP) of the patient's respiration.

While many existing differential Fick techniques provide reliable, noninvasively obtained measurements of pulmonary capillary blood flow or cardiac output, the lengths of time over which these techniques are effected are somewhat undesirable, especially in the common critical and intensive care situations in which it is desirable to more frequently update measurements of the pulmonary capillary blood flow or cardiac output of a patient.

Accordingly, there is a need for a method of noninvasively calculating pulmonary capillary blood flow and cardiac output with increased frequency.

BRIEF SUMMARY OF THE INVENTION

The present invention includes a differential Fick technique for noninvasively determining the pulmonary capillary blood flow or cardiac output of a patient. The differential Fick method of the present invention includes two phases: a "normal" respiration phase and a phase in which a change in the effective ventilation of a patient is induced, which phase is referred to herein as a "change-inducing phase." These phases are abbreviated in duration relative to similar phases in known differential Fick techniques. The phases of the inventive differential Fick technique may be repeatedly cycled, or oscillated, with the durations of the normal respiration phase and the change-inducing phase being substantially the same.

In one aspect, the inventive differential Fick technique includes effecting a change-inducing phase in the respiration of a patient, allowing the respiration of the patient to return to normal, then immediately repeating the change-inducing phase of respiration. This method differs from conventional differential Fick techniques in that the typical recovery period, where a patient's respiration is allowed to return to normal, or baseline levels before again measuring respiratory carbon dioxide and flow is omitted.

In another aspect of a differential Fick technique incorporating teachings of the present invention, the durations of the normal respiration and change-inducing phases are abbreviated relative to the time lengths of the corresponding phases in conventional differential Fick techniques. For example, each phase may have a duration of about 30 seconds. The length of an entire cycle of the differential Fick technique, measured as the difference in time between the end of one change-inducing phase and the end of another, immediately subsequent change-inducing phase is also shortened relative to the durations of conventional cycles of comparable differential Fick techniques. For example, a differential Fick technique conducted in accordance with teachings of the present invention may have a cycle time of about two minutes or less.

Teachings of the present invention may be applied to rebreathing processes, as well as other differential Fick techniques. For example, changes in the respiration rate of a patient, changes in a patient's tidal volume, changes in the inspiratory pause of a patient, and changes in the positive-end expiratory pressure of a patient each induce changes in the effective ventilation of the patient that may be used in a differential form of the Fick equation to noninvasively determine the pulmonary capillary blood flow or cardiac output of the patient.

Other features and advantages of the present invention will become apparent to those of ordinary skill in the art through consideration of the ensuing description, the accompanying drawings, and the appended claims.

BRIEF DESCRIPTION OF THE SEVERAL VIEWS OF THE DRAWINGS

In the drawings, which illustrate an exemplary embodiment for carrying out the invention.

DETAILED DESCRIPTION OF THE INVENTION

As is known in the art, due to carbon dioxide buffering and large storage volumes of carbon dioxide in the body, the $CvCO_2$ of a patient changes very slowly relative to the rate at which the $CaCO_2$ of the patient varies when a change in the effective ventilation of the patient occurs. The inability of a signal, such as the $CvCO_2$ of a patient, to respond quickly to a change in effective ventilation is referred to as "damping" of the signal.

Figure 9A:
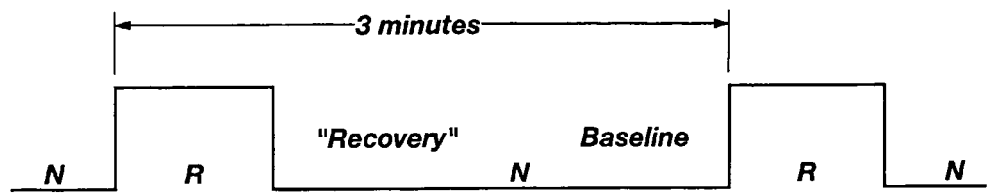
FIG. 9A schematically depicts the timing of rebreathing and nonrebreathing phases of a conventional rebreathing process.

FIG. 9A illustrates an example of a conventional rebreathing technique in which R indicates the periods during which rebreathing is effected and N designates the nonrebreathing periods, in which normal ventilation may occur. Conventional wisdom has indicated that differential Fick techniques should be short enough to avoid inducing changes in the $CvCO_2$ of a patient, but long enough to effect a substantial change in the $CaCO_2$ of the patient. Notwithstanding this conventional wisdom, it has been discovered by the inventors herein that any change in the effective ventilation of a patient sufficient to induce a change in the $CaCO_2$ of the patient without causing a significant increase in the $CvCO_2$ of the patient is useful.

Figure 9B:
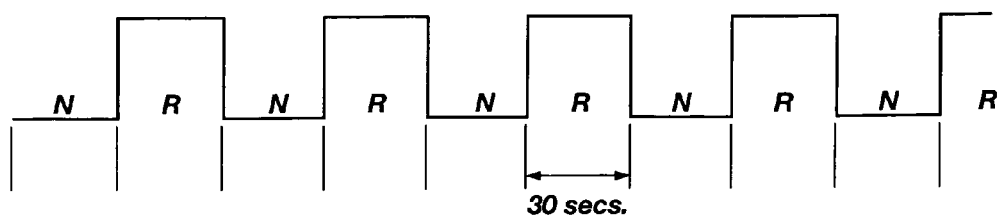
FIG. 9B schematically depicts the timing of phases of an embodiment of a method incorporating teachings of the present invention.

Accordingly, the present invention includes a method for inducing a change in the effective ventilation of a patient over a reduced period of time relative to that used in known rebreathing and other differential Fick techniques. An example of the method of the present invention is depicted in FIG. 9B. In FIG. 9B, R represents periods in which a change in the effective ventilation of a patient occurs, while N represents periods without a change in the effective ventilation of the patient, in which normal ventilation may occur. The change in effective ventilation occurs at an increased frequency relative to that at which changes in the effective ventilation of a patient are induced with previously known differential Fick techniques.

Due to the decrease in total cycle time of the inventive differential Fick technique, as well as the increased portion of the cycle in which a change in effective ventilation is induced, an initial increase in the $CvCO_2$ of a patient may occur. Following such an initial increase in the measured $CvCO_2$ of the patient, however, further changes in the effective ventilation of the patient, when conducted at a high enough frequency or oscillation rate, should not cause further, substantial changes in the $CvCO_2$ of the patient. Thus, in the differential Fick technique of the present invention, once the $CvCO_2$ of the patient reaches a new substantially steady state level, it remains at that level. Because $CvCO_2$ is damped, higher frequency changes, or oscillations, lead to a more stable $CvCO_2$.

In accordance with one aspect of the method of the present invention, a differential Fick technique may include a first phase, or ventilation state, in which a change in the effective ventilation is effected and a second phase, or ventilation state, in which "normal" ventilation, or breathing or respiration, occurs.

Of course the change between the first and second ventilation states may be either abrupt, as depicted in FIG. 9B, or gradual. For example, when the change in the effective ventilation of a patient is a change in the tidal volume of a patient, the change or oscillation between a minimum tidal volume and a maximum tidal volume may follow a sinusoidal curve (e.g., 400 ml, 410 ml, 420 ml, ... 580 ml, 590 ml, 600 ml, 590 ml, 580 ml, ... 420 ml, 410 ml, 400 m, 410 ml, 420 ml, ...).

The first and second phases, or ventilation states, of the inventive differential Fick technique may be effected for substantially the same amount of time, meaning that, while the first and second phases may have exactly the same duration, as depicted in FIG. 9B, one of the phases may alternatively be somewhat longer than the other. Either the first phase or the second phase of the differential Fick technique of the present invention may comprise as little as about 30% of the combined duration of the first and second phases or as much as about 70% of the combined duration of the first and second phases. For example, if the total cycle time of a differential Fick technique is about one minute, the first or second phase may last as little as about 18 seconds, while the other phase lasts about 42 seconds. Alternatively, the first and second phases may each last for about thirty seconds, as shown in FIG. 9B.

The durations of each of the first and second phases, or ventilation states, may be optimized for a patient by evaluating the patient's ventilation (i.e., tidal volume×frequency). Optionally, the calculated pulmonary capillary blood flow or cardiac output of the patient may be evaluated along with the patient's ventilation to determine the optimal durations for each of the first and second phases. For example, for higher cardiac output levels, it may desirable to reduce the time of each phase.

As an alternative to oscillating between first and second phases, or ventilation states, respiratory data of a patient may be monitored before noninvasively measuring pulmonary capillary blood flow or cardiac output, prior to the initiation of a change in effective ventilation that facilitates such a noninvasive measurement (e.g., during a standby period). Accordingly, pulmonary capillary blood flow or cardiac output may be measured by initiating a change in the effective ventilation of a patient (i.e., the first phase) and using data that was obtained and stored during a standby period, prior to effecting a change in the effective ventilation of a patient.

The cycle times of differential Fick techniques incorporating teachings of the present invention are preferably about two minutes or less. Cycle times of less than a minute are also within the scope of the present invention.

Another aspect of the present invention is related to a discovery of the inventors herein that, in order to accurately, noninvasively measure pulmonary capillary blood flow or cardiac output, a recovery period is not necessary following the change in the effective ventilation of the patient. Accordingly, differential Fick techniques incorporating teachings of the present invention may lack the conventional recovery or stabilization period that typically follows inducement of a change in the effective ventilation of a patient. The first and second phases may be continuously cycled, one (e.g., the first phase) immediately following completion of the other (e.g., the second phase). In addition, respiration (e.g., flow and carbon dioxide or oxygen levels) of the patient may be continuously evaluated or monitored while the differential Fick technique of the present invention is being effected. Alternatively, one or more intermittent measurements may be obtained during each immediately sequential occurrence of the first and second phases.

As an example of a differential Fick technique incorporating teachings of the present invention, partial rebreathing may be employed. In the partial rebreathing embodiment of the differential Fick technique, the first phase is a rebreathing phase, while the second phase is a nonrebreathing phase. In rebreathing, the $V_{CO_2}$ of a patient is measured along with the $PetCO_2$ of the patient or another indicator of the carbon dioxide content of the patient's blood (e.g., $CaCO_2$, $pCO_2$, a surrogate of $PetCO_2$, such as the average $pCO_2$ over about the last 5% of the expired volume, etc.).

Figure 1:
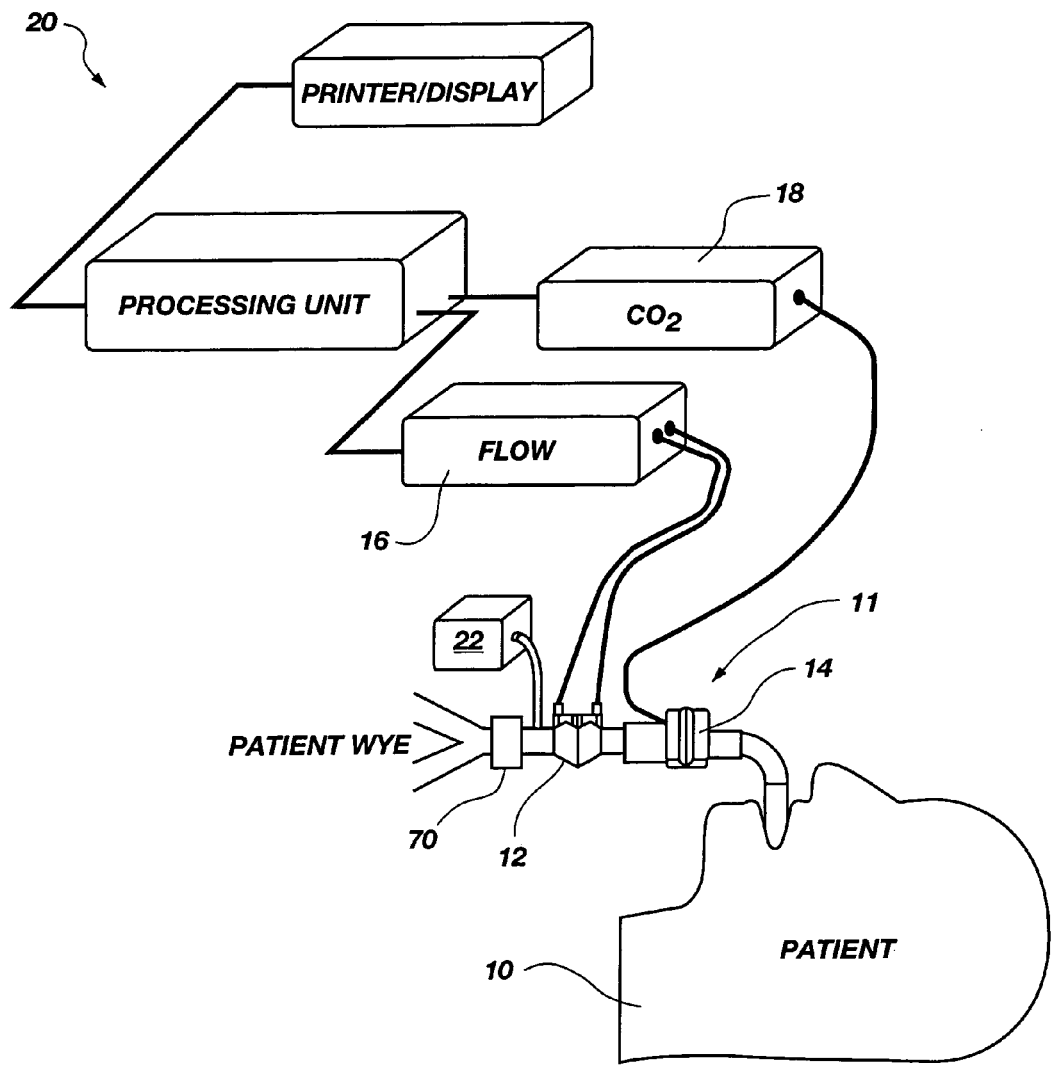
FIG. 1 is a schematic representation which illustrates the componentry that may be utilized to measure respiratory profile parameters in a method incorporating teachings of the present invention.

FIG. 1 schematically illustrates an exemplary method of substantially noninvasively monitoring the respiration of a patient and of measuring the flow rates and carbon dioxide concentration of gas mixtures that are inhaled and exhaled by a patient 10 over the course of the patient's breathing, such as during normal respiration or during known rebreathing techniques. A respiratory circuit 11 is placed in communication with the airway of patient 10. A flow sensor 12 of a known type, such as the differential-pressure type respiratory flow sensors manufactured by Novametrix Medical Systems Inc. ("Novametrix") of Wallingford, Conn. (e.g, the Pediatric/Adult Flow Sensor (Catalog No. 6717) or the Neonatal Flow Sensor (Catalog No. 6718)), is positioned along ventilation circuit 11. Flow sensor 12 may be operatively attached to a ventilation apparatus (not shown) or patient breathing mask or mouthpiece, as well as respiratory flow sensors based on other operating principles and manufactured or marketed by others, may be used to measure the flow rates of the breathing of patient 10.

A carbon dioxide sensor 14, such as the CAPNOSTAT® carbon dioxide sensor and a complementary airway adapter (e.g., the Pediatric/Adult Single Patient Use Airway Adapter (Catalog No. 6063), the Pediatric/Adult Reusable Airway Adapter (Catalog No. 7007), or the Neonatal/Pediatric Reusable Airway Adapter (Catalog No. 7053)), which are manufactured by Novametrix, as well as main stream and side stream carbon dioxide sensors manufactured or marketed by others, may be positioned along ventilation circuit 11 so as to measure the carbon dioxide concentration of gas mixtures that are inhaled and exhaled by patient 10.

Flow sensor 12 and carbon dioxide sensor 14 are connected to a flow monitor 16 and a carbon dioxide monitor 18, respectively, each of which may be operatively associated with a computer 20 so that data from the flow and carbon dioxide monitors 16 and 18 representative of the signals from each of flow sensor 12 and carbon dioxide sensor 14 may be detected by computer 20 and processed according to programming (e.g., by software) thereof. Preferably, raw flow and carbon dioxide signals from flow monitor 16 and carbon dioxide sensor 14 are filtered to remove any significant artifacts. As respiratory flow and carbon dioxide pressure measurements are made, the respiratory flow and carbon dioxide pressure data may be stored by computer 20.

Each breath, or breathing cycle, of patient 10 may be delineated, as known in the art, such as by continuously monitoring the flow rate of the breathing of patient 10.

In order to effect rebreathing, a deadspace 22, or carbon dioxide source, communicates with the airway of patient 10. During the nonrebreathing phase, communication between deadspace 22 and the airway of patient 10 is interrupted.

In partial rebreathing in accordance with teachings of the present invention, a baseline may be established during the nonrebreathing phase, in which carbon dioxide elimination and the partial pressure of end tidal carbon dioxide are measured. The nonrebreathing phase is then immediately followed by a rebreathing phase, wherein a change in the $CaCO_2$ of the patient is induced and $V_{CO_2}$ and $PetCO_2$ are again measured. The rebreathing phase is then immediately followed by another nonrebreathing phase, wherein $V_{CO_2}$ and $PetCO_2$ are again measured.

The differential Fick technique of the present invention may be used with conventional rebreathing maneuvers and processes, as well as other known rebreathing maneuvers and processes, which are modified by either shortening or completely eliminating the conventional recovery or stabilization periods of these maneuvers and processes. For example, the differential Fick technique of the present invention may be used with the so-called "bi-directional" process disclosed in U.S. patent application Ser. No. 09/150,136, filed Sep. 9, 1998, now U.S. Pat. No 6,238,351, issued May 29, 2001 (hereinafter "the '351 Patent"), the disclosure of which is hereby incorporated in its entirety by this reference, or in the so-called "best-fit line" method, which is disclosed in U.S. patent application Ser. No. 09/510,702, filed on Feb. 22, 2000, now U.S. Pat. No. 6,540,689, issued Apr. 1, 2003 (hereinafter "the '689 Patent"), the disclosure of which is hereby incorporated in its entirety by this reference.

Bi-directional Rebreathing

In the bi-directional rebreathing process, as disclosed in the '351 Patent, respiratory carbon dioxide and flow measurements are obtained in three phases: a "before" rebreathing phase, a "during" rebreathing phase, and an "after" rebreathing phase. When teachings of the present invention are applied to the bi-directional rebreathing method, measurements obtained during a first nonrebreathing phase provide data for the "before" rebreathing period of a first rebreathing cycle, measurements obtained in the rebreathing phase provide data for the "during" rebreathing period of the first rebreathing cycle, and measurements obtained during the next nonrebreathing phase provide data for both the "after" rebreathing period of the first rebreathing cycle and the "before" rebreathing period of the next rebreathing cycle.

In a first variation of the bi-directional rebreathing technique, which is useful when the $CvCO_2$ of a patient is changing, the rate at which the $CvCO_2$ changes is estimated, which may be useful for more accurately determining the pulmonary capillary blood flow or cardiac output of the patient. The rate of change in $CvCO_2$ may also be used to determine the rate or amount of change in the $CvCO_2$ of the patient between "normal" respiration and the change in effective ventilation. In a second variation of the bi-directional rebreathing technique, the pulmonary capillary blood flow or cardiac output of a patient may be determined without estimating the rate of change in $CvCO_2$. The second variation of the bi-directional rebreathing technique is also useful for determining the pulmonary capillary blood flow or cardiac output of a patient when either $CvCO_2$ or cardiac output changes during the re-breathing process.

Derivation of Formulae Employed in the Bi-directional Rebreathing Technique

A differential form of the carbon dioxide Fick equation, similar to that employed in conventional partial re-breathing techniques, which is based on $V_{CO_2}$ and $CvCO_2$ during "normal" respiration (B) and during the rebreathing process (Q), follows:

$$Q_{BD} = \frac{V_{CO_{2B}} - V_{CO_{2D}}}{(C_V CO_{2B} - C_V CO_{2D}) - (C_A CO_{2B} - C_A CO_{2D})} \quad (5)$$

or $$Q_{BD} = \frac{\Delta V_{CO_{2BD}}}{\Delta C_V CO_{2BD} - \Delta C_A CO_{2BD}} \quad (6)$$

Similarly, another differential form of the carbon dioxide Fick equation, which is based on carbon dioxide elimination and carbon dioxide content measurements made during the rebreathing process and after rebreathing, which may also be employed to determine the pulmonary capillary blood flow or cardiac output of a patient, follows:

$$Q_{DA} = \frac{V_{CO_{2D}} - V_{CO_{2A}}}{(C_V CO_{2D} - C_V CO_{2A}) - (C_A CO_{2D} - C_A CO_{2A})} \quad (7)$$

or $$Q_{DA} = \frac{\Delta V_{CO_{2DA}}}{\Delta C_V CO_{2DA} - \Delta C_A CO_{2DA}}, \quad (8)$$

where $CvCO_{2A}$ is the $CvCO_2$ of the patient after rebreathing (A), or in the "after" phase.

The two preceding differential forms of the carbon dioxide Fick equation may be combined to yield the following differential form of the carbon dioxide Fick equation:

$$Q = \frac{\Delta V_{CO_{2BD}} - \Delta V_{CO_{2DA}}}{(\Delta C_V CO_{2BD} - \Delta C_V CO_{2DA}) - (\Delta C_A CO_{2BD} - \Delta C_A CO_{2DA})}. \quad (9)$$

Since $CvCO_2$ may change over time, an accurate noninvasive Fick-based determination of the pulmonary capillary blood flow or cardiac output of a patient may include an estimation of the rate at which $CvCO_2$ changes. With an exemplary assumption that changes in $CvCO_2$ are substantially linear over the rebreathing cycle and, therefore, that the rate of change is constant, the rate of change in $CvCO_2$, represented as "k," may be determined with the following equation:

$$k = \frac{\Delta C_V CO_2}{\Delta t}. \quad (10)$$

Alternatively, the change in carbon dioxide content of the venous blood may be assumed to substantially follow a curve of some other shape that is reasonably based on the character of the change in carbon dioxide content, such as an exponential curve, wherein the rate of change would also be exponential, or the curve of a polynomial. As another alternative, the rate of change in $CvCO_2$ may be approximated by an artificial neural network or a radial basis function, as known in the art.

When the change in $CvCO_2$ is assumed to be linear with respect to time and, therefore, the rate of change of $CvCO_2$ is assumed to be constant, the change in $CvCO_2$ between the "before" and "during" phases and between the "during" and "after" phases can be expressed by the following equations:

$$\Delta CvCO_{2BD} = k(t_B - t_D) \quad (11)$$

and $$\Delta CvCO_{2DA} = k(t_D - t_A), \quad (12)$$

where $t_D$, $t_B$ and $t_A$ represent the times at which the "before," "during" and "after" phases respectively occur.

The foregoing equations for the change in $CvCO_2$ may be substituted into the differential form of the carbon dioxide Fick equation that considers the breathing of a patient during each of the "before," "during" and "after" phases and the "$\Delta$" terms expanded to yield the following form of the carbon dioxide Fick equation, which accounts for any changes in $CvCO_2$ and is, therefore, useful in the bi-directional rebreathing method:

$$Q = \frac{V_{CO_{2B}} + V_{CO_{2A}} - 2 \cdot V_{CO_{2D}}}{k \cdot (t_B + t_A - 2 \cdot t_D) - (C_A CO_{2B} + C_A CO_{2A} - 2 \cdot C_A CO_{2D})}. \quad (13)$$

If, however, $t_D - t_B = t_A - t_D$ as is probable in the differential Fick technique of the present invention, then $t_A + t_B = 2 \cdot t_D$, and it would not be necessary to calculate k, as k would be multiplied by zero. Accordingly, if $t_D - t_B = t_A - t_D$, such as when the durations of the first and second phases are the same, the following equation could be employed to determine the pulmonary capillary blood flow of a patient:

$$Q = \frac{V_{CO_{2B}} + V_{CO_{2A}} - 2 \cdot V_{CO_{2D}}}{-(C_A CO_{2B} + C_A CO_{2A} - 2 \cdot C_A CO_{2D})}. \quad (14)$$

Due to the assumption that the pulmonary capillary blood flow and cardiac output of a patient remain substantially constant from the "before" phase to the "after" phase, the differential carbon dioxide Fick equations for determining pulmonary capillary blood flow or cardiac output over the "before" and "during" phases ($Q_{BD}$) and for determining cardiac output over the "during" and "after" phases ($Q_{DA}$) may be employed to estimate k, the rate of change in $CvCO_2$, as follows:

$$Q_{BD} = Q_{DA}, \quad (15)$$

thus, $$\frac{\Delta V_{CO_{2BD}}}{\Delta C_V CO_{2BD} - \Delta C_A CO_{2BD}}, = \frac{\Delta V_{CO_{2DA}}}{\Delta C_V CO_{2DA} - \Delta C_A CO_{2DA}}, \quad (16)$$

which may be rearranged as:

$$\Delta V_{CO_{2BD}} \cdot \Delta C_V CO_{2DA} - \Delta V_{CO_{2DA}} \cdot \Delta C_V CO_{2BD} = \Delta V_{CO_{2BD}} \cdot \Delta C_A CO_{2DA} - \Delta V_{CO_{2DA}} \cdot \Delta C_A CO_{2BD}. \quad (17)$$

The equations for $\Delta CvCO_{2BD}$ (11) and $\Delta CvCO_2$ DA (12) are then substituted into the preceding equation (17) to yield the following equation:

$$\Delta V_{CO_{2BD}} \cdot k(t_D - t_A) - \Delta V_{CO_{2DA}} \cdot k(t_B - t_D) = \Delta V_{CO_{2BD}} \cdot \Delta C_A CO_{2DA} - \Delta V_{CO_{2DA}} \cdot \Delta C_A CO_{2BD}, \quad (18)$$

which may be rearranged to provide the following equation for k, the rate of change in $V_{CO_2}$:

$$k = \frac{\Delta V_{CO_{2BD}} \cdot \Delta C_A CO_{2DA} - \Delta V_{CO_{2DA}} \cdot \Delta C_A CO_{2BD}}{\Delta V_{CO_{2BD}}(t_D - t_A) - \Delta V_{CO_{2DA}}(t_B - t_D)}. \quad (19)$$

Use of the Bi-directional Rebreathing Technique While Cardiac Output is Changing to Noninvasively Determine Pulmonary Capillary Blood Flow Equation (14) above may also used to determine the pulmonary capillary blood flow or cardiac output of a patient if the pulmonary capillary blood flow or cardiac output of the patient changes during the bi-directional rebreathing process. This can be shown by assuming that $CvCO_2$ does not change during re-breathing:

$$CvCO_2 = CvCO_{2B} = CvCO_{2D} = CvCO_{2A}. \quad (20)$$

The Fick equation can be used to express $V_{CO_2}$ in terms of $CvCO_2$ and $CaCO_2$ or $C_A CO_2$ during each of the before, during, and after phases of the bi-directional partial rebreathing method:

$$V_{CO_{2B}} = Q_B(CvCO_{2B} - C_A CO_{2B}); \quad (21)$$

$$V_{CO_{2D}} = Q_D(CvCO_{2D} - C_A CO_{2D}); \text{ and} \quad (22)$$

$$V_{CO_{2A}} = Q_A(CvCO_{2A} - C_A CO_{2A}). \quad (23)$$

Substituting equations (21)–(23) for the $V_{CO_{2B}}$, $V_{CO_{2D}}$, and $V_{CO_{2A}}$ terms of equation (14) along with the assumption that $CvCO_2$ is not changing during rebreathing in equation (20) provides the following equation:

$$Q = \frac{Q_B(C_VCO_2 - C_ACO_{2B}) + Q_D(C_VCO_2 - C_ACO_{2D}) - 2Q_A(C_VCO_2 - C_ACO_{2A})}{-(C_ACO_{2B} + C_ACO_{2A} - 2 \cdot C_ACO_{2D})}. \quad (24)$$

When it is assumed that $CvCO_2$ does not change during rebreathing, it may be implied that once the rebreathing process is stopped, $CaCO_2$ and $C_ACO_2$ return to substantially the same levels of these parameters prior to the rebreathing process, or the same levels of these parameters if rebreathing had not been conducted or another change in the ventilation of a patient had not been induced:

$$C_ACO_{2B} = C_ACO_{2A} = C_ACO_{2NR}, \quad (25)$$

where $C_ACO_{2NR}$ is the content of carbon dioxide in the capillaries surrounding the alveoli during time periods in which a change in the ventilation of a patient has not been induced (e.g., as is induced during rebreathing), such as during the second phase of the differential Fick technique of the present invention. Thus, $C_ACO_{2NR}$ may be substituted for both $C_ACO_{2B}$ and $C_ACO_{2A}$ in equation (24), providing the following equation:

$$Q = \frac{Q_B \cdot CvCO_2 - Q_B \cdot CACO_{2NR} + Q_A \cdot CvCO_2 - Q_A \cdot CACO_{2NR} - 2Q_D \cdot CvCO_2 + Q_D \cdot CACO_{2D}}{-2(CACO_{2NR} - CACO_{2D})}. \quad (26)$$

By factoring certain terms, equation (26) can be rewritten as follows:

$$Q = \frac{(Q_B + Q_A - 2Q_D) \cdot CvCO_2 - (Q_A + Q_B) \cdot CACO_{2NR} + 2Q_D \cdot CACO_{2D}}{-2(CACO_{2NR} - CACO_{2D})}. \quad (27)$$

If it is assumed that the pulmonary capillary blood flow or the cardiac output of the patient changes linearly over time, or that the difference in pulmonary capillary blood flow or cardiac output between before and during phases of the bi-directional partial rebreathing method is equal to the difference in pulmonary capillary blood flow or cardiac output between the during and after phases, then the pulmonary capillary blood flow or cardiac output of the patient in the during phase of rebreathing may be expressed by the following equation:

$$Q_D = \tfrac{1}{2}(Q_A + Q_B), \quad (28)$$

Substituting equation (28) into equation (27) provides the following equation:

$$Q = [Q_A + Q_B - (Q_A + Q_B)] \cdot \frac{CvCO_2 - (Q_A + Q_B) \cdot CACO_{2NR} + 2CACO_{2D}}{-2(CACO_{2NR} - CACO_{2D})}(QA + QB), \quad (29)$$

which is the equivalent of the following equation:

$$Q = \tfrac{1}{2}(Q_A + Q_B), \quad (30)$$

which is equal to $Q_D$.

Thus, when the pulmonary capillary blood flow or cardiac output of a patient changes at a constant rate during the bi-directional partial rebreathing method, the cardiac output or pulmonary capillary blood flow of a patient is equal to the pulmonary capillary blood flow or cardiac output of the patient as measured in the during phase of partial rebreathing. Accordingly, equations (13) and (14) may be used with the bi-directional partial rebreathing process to accurately and noninvasively determine the pulmonary capillary blood flow or the cardiac output of a patient while the pulmonary capillary blood flow or cardiac output of the patient is changing.

The bi-directional partial rebreathing method, as embodied in equations (13) and (14), may also be useful for noninvasively determining the pulmonary capillary blood flow or cardiac output of a patient while both the $CvCO_2$ and the pulmonary capillary blood flow or cardiac output of the patient are changing.

In practicing the bi-directional rebreathing method, a system such as that described in reference to FIG. 1 is used and the patient's breathing is monitored during rebreathing and nonrebreathing phases to detect the amount of $CO_2$ exhaled by the patient and the flow rate of the patient's respiration during these phases, from which $V_{CO_2}$ and $CvCO_2$ may be determined.

Figure 2A:
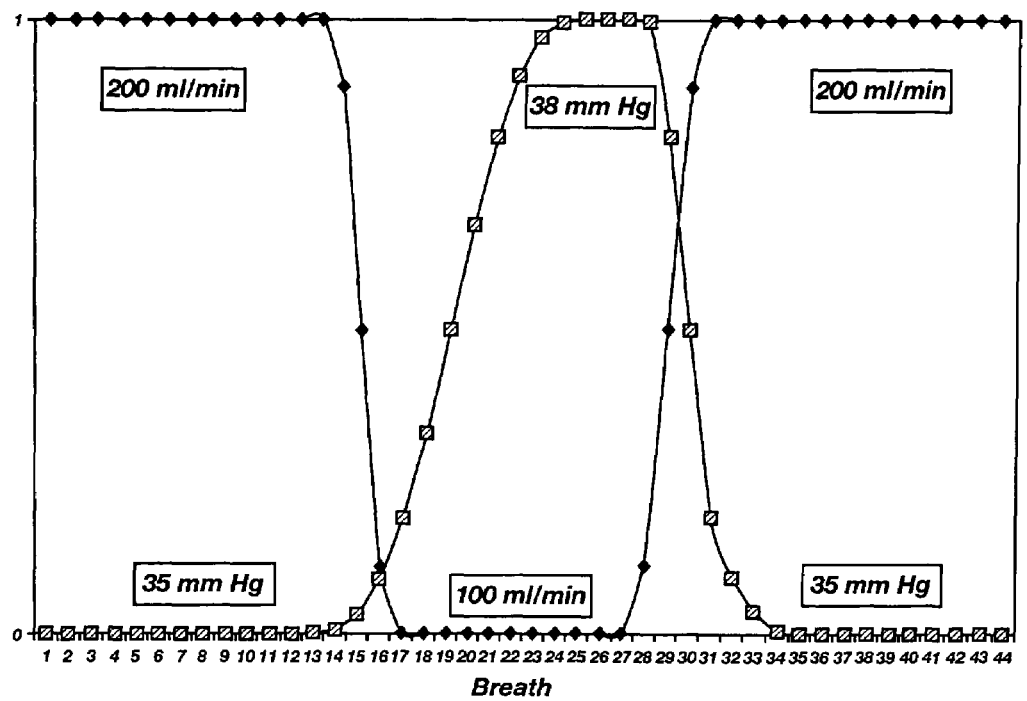
FIG. 2A illustrates an idealized, bi-directional rebreathing cycle with $V_{CO_2}$ values for different breaths depicted as diamonds and $PetCO_2$ values for various breaths shown as squares.

The graph of FIG. 2A illustrates the various measurements that may be obtained during bi-directional rebreathing. As illustrated, the typical changes in the $V_{CO_2}$ (shown as diamonds) and carbon dioxide content measurements (e.g., $PetCO_2$, shown as squares) that may occur between the baseline breathing (i.e., "before" rebreathing), "during" rebreathing, and the recovery or stabilization (i.e., "after" rebreathing) periods of an idealized (i.e., without noise) bi-directional rebreathing cycle. During rebreathing, $V_{CO_2}$ changes from a baseline value (e.g., about 200 ml/min) to a during rebreathing plateau (e.g., of about 100 ml/min.) within about 3 or 4 breaths, whereas carbon dioxide content may take longer to change from a baseline value (e.g., 35 mmHg) to a plateau (e.g., about 39 mmHg).

Figure 2B:
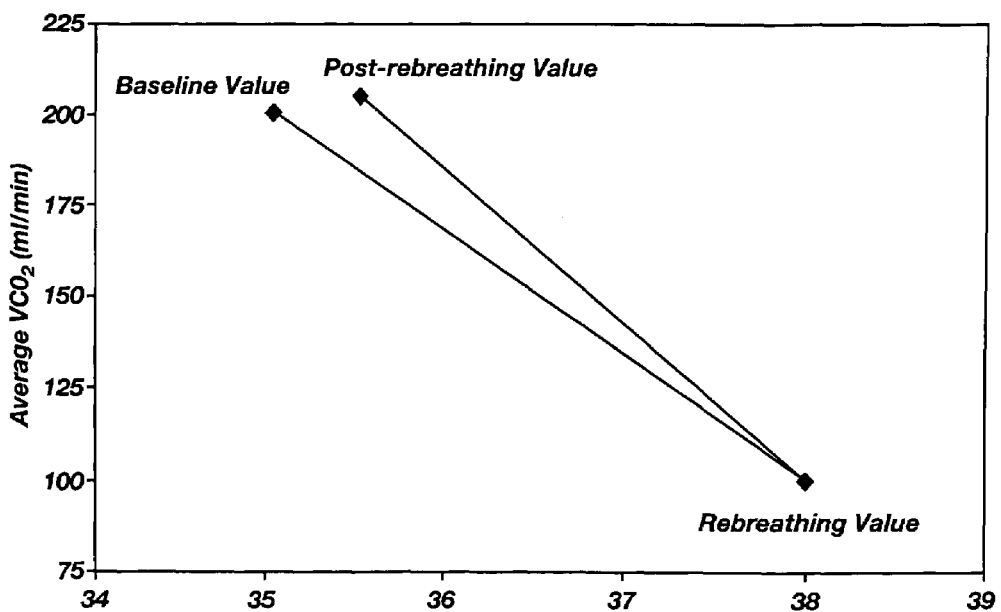
FIG. 2B is a two-dimensional plot illustrating the use of a bi-directional rebreathing process to obtain three $V_{CO_2}$ values and three values representative of the carbon dioxide content of the blood of a patient before, during, and after rebreathing; these three values have been used to substantially noninvasively determine the pulmonary capillary blood flow or cardiac output of the patient.

FIG. 2B is a two-dimensional plot that illustrates that single values, the plateau values, from each of the before, during, and after rebreathing phases of a bi-directional rebreathing process, such as that illustrated in FIG. 2A, are used to estimate pulmonary capillary blood flow or cardiac output.

Figure 3:
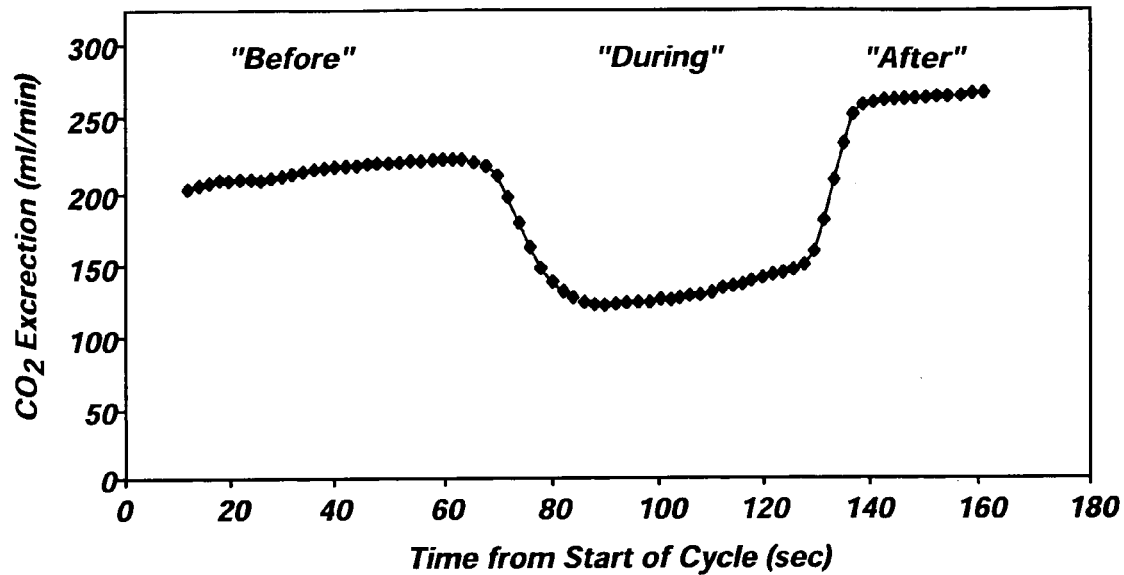
FIG. 3 is a line graph that illustrates the $V_{CO_2}$ of a patient during each of the before, during, and after phases of the bi-directional rebreathing method.

The difference between the volume of carbon dioxide exhaled and the volume of carbon dioxide inhaled by a patient, which may be used to estimate the $V_{CO_2}$ of the patient, is determined before ($V_{CO_{2B}}$), during ($V_{CO_{2D}}$), and after ($V_{CO_{2A}}$) rebreathing. FIG. 3 is a graph that illustrates $V_{CO_2}$ during each of the before, during, and after phases of the rebreathing process of the present invention.

Figure 4:
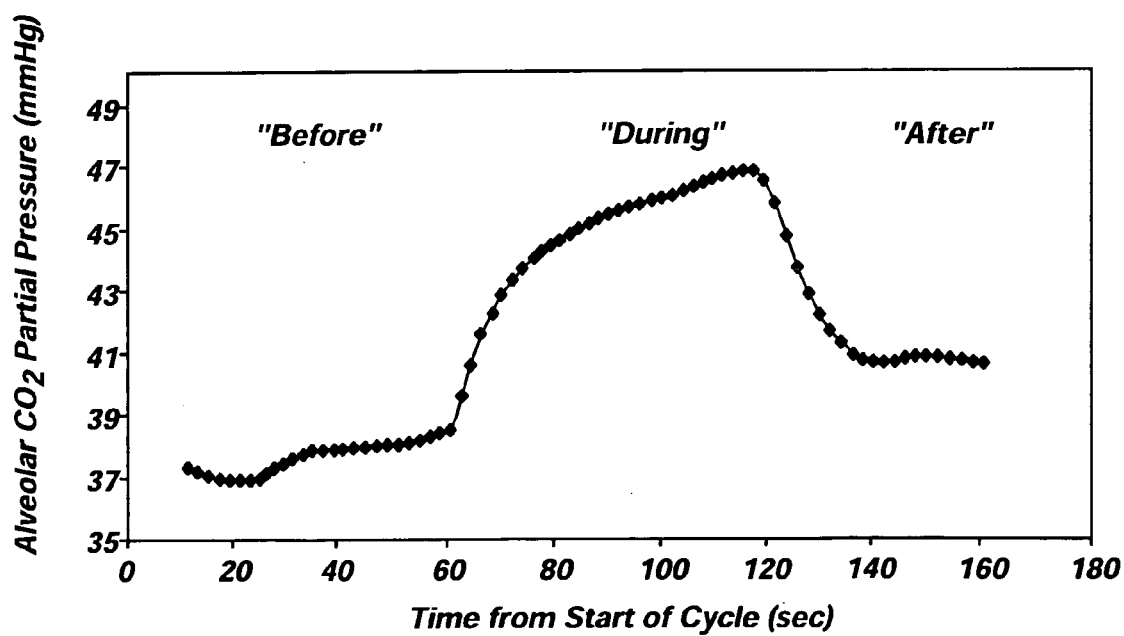
FIG. 4 is a line graph that illustrates the $PetCO_2$ of a patient during each of the before, during, and after phases of the bi-directional rebreathing method.

The $PetCO_2$ of the patient is also measured for each of the "before," "during" and "after" phases. As $PetCO_2$, when corrected for parallel deadspace (of non-perfused alveoli), is assumed to be equal to the partial pressure of carbon dioxide in the alveolar blood ($PACO_2$) and the partial pressure of $CO_2$ in the arterial blood ($PaCO_2$), a carbon dioxide dissociation curve may be employed with the end tidal carbon dioxide partial pressure measurements, as known in the art, to determine the content of carbon dioxide in blood of the alveoli ($CACO_2$) of the lungs of the patient that participate in the exchange of blood gases, which alveoli are typically referred to as "perfused" alveoli, for each of the before, during, and after rebreathing phases. $C_ACO_2$ is assumed to be equal to the content of carbon dioxide in the arterial blood ($CaCO_2$). FIG. 4 is a graph that illustrates the $PetCO_2$ measured during each of the before, during, and after phases of the rebreathing process of the present invention.

Determining Pulmonary Capillary Blood Flow or Cardiac Output

In determining the pulmonary capillary blood flow or cardiac output of a patient when $CvCO_2$ changes, the differences between $V_{CO_2}$ before rebreathing and during rebreathing, which difference is also referred to as "$\Delta V_{CO_{2BD}}$," and during rebreathing and after rebreathing, which difference is also referred to as "$\Delta V_{CO_{2DA}}$," are determined. The differences between the $C_ACO_2$ before and during rebreathing, which difference is also referred to as "$\Delta C_ACO_{2BD}$," and during rebreathing and after rebreathing, which difference is also referred to as "$\Delta C_ACO_{2DA}$," are also determined.

These differences may then be used to calculate the rate at which the content of carbon dioxide in the venous blood of the patient changes. An exemplary equation for estimating the rate of change in the content of carbon dioxide in the patient's venous blood (k), which assumes that the change is linear with time and, therefore, that the rate of change is constant, follows:

$$k = \frac{\Delta VCO_{2BD} \cdot \Delta CACO_{2DA} - \Delta VCO_{2DA} \cdot \Delta CACO_{2BD}}{\Delta VCO_{2BD}(t_D - t_A) - \Delta VCO_{2DA}(t_B - t_D)}. \tag{31}$$

Once the rate of change in the content of carbon dioxide in the patient's blood has been estimated, the pulmonary capillary blood flow or cardiac output of the patient may be accurately determined, as follows:

$$Q = \frac{VCO_{2B} + VCO_{2A} - 2VCO_{2D}}{k \cdot (t_B + t_A - 2t_D) - (CACO_{2B} + CACO_{2A} - 2CACO_{2D})} \tag{32}$$

Alternatively, the times and constant may be omitted from the previous equation and pulmonary capillary blood flow or cardiac output of the patient determined by use of the following equation, which is useful when either $CvCO_2$ or pulmonary capillary blood flow or cardiac output changes during re-breathing:

$$Q = \frac{VCO_{2B} + VCO_{2A} - 2VCO_{2D}}{-(CACO_{2B} + CACO_{2A} - 2CACO_{2D})}. \tag{33}$$

Best-Fit Line Method

By way of contrast with the use of measurements at the plateaus of each of the phases, as depicted in FIGS. 2A and 2B, in conventional rebreathing processes and the bi-directional rebreathing process, $V_{CO_2}$ and carbon dioxide content data are continually measured in the rebreathing method of the '689 Patent. As a result, a plot of the measurements may have the appearance of the graph shown in FIG. 5A, with data at 100 being based on before rebreathing measurements, data along arrow 102 being based on during rebreathing measurements, and data along arrow 104 being based on after rebreathing measurements. These data may be obtained by use of a single rebreathing cycle, over the course of a number of rebreathing cycles, at one or more discrete time intervals, or on a breath-by-breath basis, where data is continually measured, calculated, and analyzed in accordance with the method of the invention so as to continually update or monitor the pulmonary capillary blood flow or cardiac output of a patient.

The best-fit line method also includes use of a differential form of the carbon dioxide Fick equation to calculate pulmonary capillary blood flow or cardiac output as the ratio of a change in carbon dioxide elimination, or $V_{CO_2}$, to a change in the content of carbon dioxide, or $CaCO_2$, in the arterial blood of a patient:

$$Q = \frac{\Delta VCO_2}{\Delta CaCO_2}. \tag{34}$$

As explained previously herein, $CaCO_2$ can be noninvasively estimated by determining the $PetCO_2$. $PetCO_2$ may be converted to $CaCO_2$ by use of a standard carbon dioxide dissociation curve, as is known in the art, by use of the following equation:

$$\Delta CaCO_2 = s\Delta Pet\, CO_2, \tag{35}$$

where s is the slope of the carbon dioxide dissociation curve and $\Delta PetCO_2$ is a change in the end tidal partial pressure of carbon dioxide of a patient effected by a change in ventilation. Thus, pulmonary capillary blood flow or cardiac output can also be calculated as follows:

$$Q = \Delta V_{CO_2}/s\Delta PetCO_2. \tag{36}$$

Other indicators of the carbon dioxide content in the blood of a patient, such as $pCO_2$, may be used in place of $PetCO_2$ or $CaCO_2$ to determine the pulmonary capillary blood flow or cardiac output of a patient.

Once respiratory carbon dioxide pressure and flow measurements have been made, as depicted in FIG. 1, during both the first (e.g., rebreathing) and second (e.g., nonrebreathing) phases, these respiratory carbon dioxide pressure and flow data are used, as known in the art, to calculate $V_{CO_2}$ and $PetCO_2$, as well as the changes in $V_{CO_2}$ and $PetCO_2$ that occur with the change in effective ventilation.

The calculated $V_{CO_2}$ and $PetCO_2$ data are then used to determine the pulmonary capillary blood flow or cardiac output of the patient, such as by use of any of the various Fick equations presented above.

As an alternative, the pulmonary capillary blood flow or cardiac output of a patient can be determined over the course of a plurality of breaths by expressing the calculated $V_{CO_2}$ data and $CaCO_2$ data or data of another indicator of the content of carbon dioxide in the blood of a patient, such as $PetCO_2$ or $pCO_2$, in two dimensions, such as on a two-dimensional (X-Y) line graph, with $V_{CO_2}$ data points being measured on the y-axis and $PetCO_2$ data points being measured on the x-axis, then identifying a line that best fits the data, which is also referred to herein as a best-fit line.

For example, the equation for the best-fit line is:

$$y = mx + b \tag{37}$$

or $$m = \frac{y - b}{x}, \tag{38}$$

where y is the y-axis ordinate of a data point, x is the x-axis ordinate of the same data point, m is the slope of the line, and b is the offset value for the line. If $V_{CO_2}$ is measured on the y-axis and $CaCO_2$ is measured on the x-axis, then $$m = \frac{VCO_2 - b}{CaCO_2}. \tag{39}$$

The negative slope (i.e., $-1 \times m$) of the best-fit line through the $V_{CO_2}$–$CaCO_2$ data would be equal to the pulmonary capillary blood flow or cardiac output of the patient:

$$-m=Q. \tag{40}$$

The best-fit line for the $V_{CO_2}$ and $CaCO_2$ data is preferably determined by use of known linear regression techniques or any other known methodology for determining the relationship between two variables. The method of linear regression provides an accurate pulmonary capillary blood flow or cardiac output value based on a large number of $V_{CO_2}$ and $CaCO_2$ data obtained over the course of one or more changes in effective ventilation. When linear regression is used, the slope (m) of the best-fit line for the data is calculated as follows:

$$m = Lxy/Lxx \tag{41}$$

and the offset (b) of the line is calculated by the following equation:

$$b = \Sigma y/n - m \times \Sigma x/n, \tag{42}$$

where $$Lxx = \Sigma x^2 - (\Sigma x \times \Sigma x)/n, \tag{43}$$

$$Lyy = \Sigma y^2 - (\Sigma y \times \Sigma y)/n, \text{ and} \tag{44}$$

$$Lxy = \Sigma xy - (\Sigma x \times \Sigma y)/n, \tag{45}$$

and where n is the number of data points in the plot, $\Sigma x$ is the sum of all x-ordinate (i.e., $CaCO_2$ content) values, $\Sigma y$ is the sum of all y-ordinate (i.e., $V_{CO_2}$) values, $\Sigma x^2$ is the sum of the square of all x-ordinate values, $\Sigma y^2$ is the sum of the square of all y-ordinate values, and $\Sigma xy$ is the sum all paired x- and y-ordinate values multiplied by each other.

When linear regression is used to determine the location and orientation of a best-fit line, a correlation coefficient (r) that quantifies the accuracy with which the best-fit line correlates to the $V_{CO_2}$ and $CaCO_2$ data can also be calculated as follows:

$$r = (Lxy \times Lxy)/(Lyy \times Lxx). \tag{46}$$

Alternatively, any other measure of the quality of fit that quantifies the accuracy with which the best-fit line correlates to the $V_{CO_2}$ and $CaCO_2$ data may be used.

Correlation coefficients range from 0 to 1.0, where a correlation coefficient of 0 indicates that no linear correlation exists between the x-ordinate and the y-ordinate data and a correlation coefficient of 1.0 indicates that the x-ordinate and y-ordinate data are perfectly linearly correlated (i.e., all of the $V_{CO_2}$–$CaCO_2$ data points are located on the same straight line).

Figure 5A:
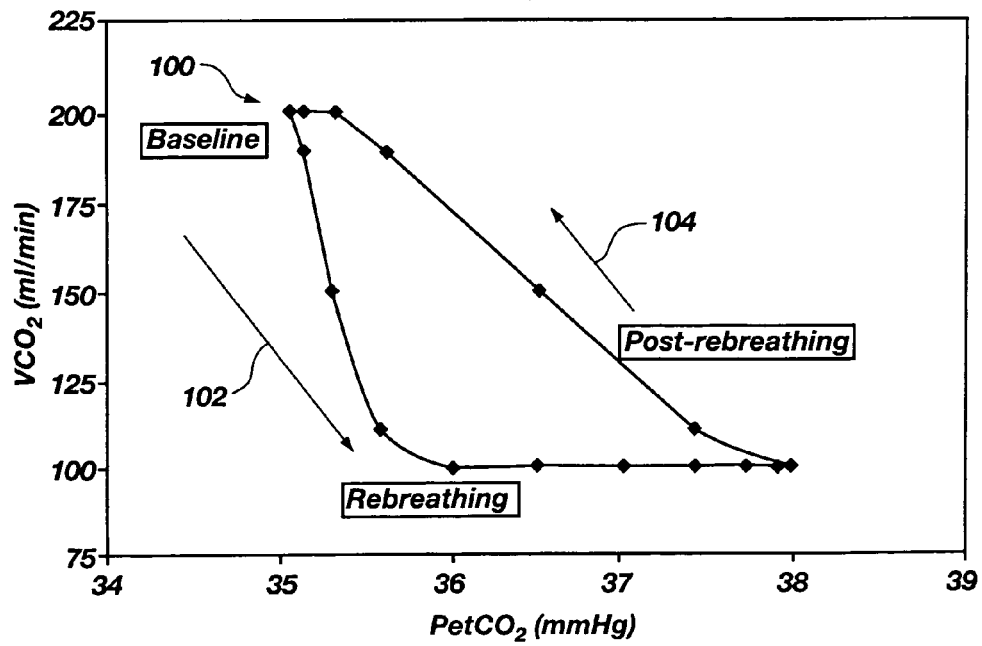
FIG. 5A is a two-dimensional line graph illustrating a typical plot of $V_{CO_2}$ on the y-axis and $PetCO_2$ on the x-axis.
Figure 6:
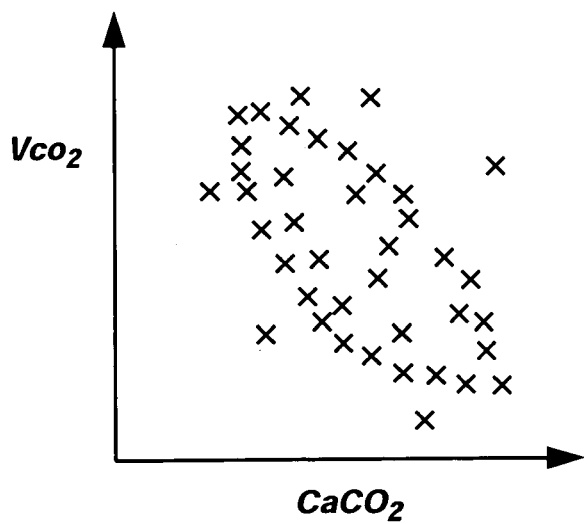
FIG. 6 is a two-dimensional plot of a number of $V_{CO_2}$ values against the same number of carbon dioxide content values obtained over a single bi-directional rebreathing cycle.

The $V_{CO_2}$–$CaCO_2$ data points measured before and during rebreathing, however, are rarely located on the same straight line. One reason for this is that, during rebreathing maneuvers, the $V_{CO_2}$ signal typically leads the $PetCO_2$ signal and, thus, the $CaCO_2$ by about one breath. In addition, $V_{CO_2}$ is calculated on the basis of signal components that have higher frequencies than do the $PetCO_2$ signal. As a result, when the $V_{CO_2}$ and $CaCO_2$ measurements calculated over a period of time are plotted against one another on a two-dimensional (X-Y) line graph, the result typically appears as an arc or a loop, as shown in FIGS. 5A and 6, rather than as a straight line, depending on the amount of data calculated and the duration of rebreathing. Moreover, $V_{CO_2}$ and $CaCO_2$ measurements may be calculated on the basis of respiratory flow and carbon dioxide pressure data obtained during spurious breaths. Such data do not relate to the pulmonary capillary blood flow or cardiac output measurement. $V_{CO_2}$ and $CaCO_2$ calculations that are based upon such spurious data act as noise that may result in miscalculation of a best-fit line through the calculated $V_{CO_2}$ and $CaCO_2$ data. As a result, the correlation coefficient of a best-fit line to the data is typically much less than 1.0.

The measured respiratory flow and carbon dioxide pressure data or the calculated $V_{CO_2}$ and $CaCO_2$ data can be modified to increase the correlation coefficient between the $V_{CO_2}$ and $CaCO_2$ data and the best-fit line therefor. Preferably, a linear transform is used to increase the correlation coefficient. A linear transform may be used to delay the calculation of a $V_{CO_2}$ data point to accurately coincide therewith a $CaCO_2$ data point based on measurements taken during the same breath. The measured or calculated data may also be filtered by use of a linear transform.

In an exemplary method for increasing the correlation coefficient between the $V_{CO_2}$ and $CaCO_2$ data and the best-fit line therefor, a filter is applied to the calculated $V_{CO_2}$ or $CaCO_2$ data. Known analog or digital low-pass, high-pass, or band pass filters, including adaptive filters, may be employed. Linear or nonlinear filters may be used. Preferably, a first order (single pole) infinite impulse response (IIR) digital filter is employed to filter the $V_{CO_2}$ calculations in a manner that improves the correlation between the $V_{CO_2}$ calculation and the lagging $PetCO_2/CaCO_2$ calculation. The equation for such a filter is:

$$V_{CO_2}'[n] = \alpha \times V_{CO_2}'[n-1] + (1-\alpha) \times V_{CO_2}[n], \tag{47}$$

where $V_{CO_2}[n]$ is the most recently calculated, unfiltered $V_{CO_2}$ data point, $V_{CO_2}'[n-1]$ is the previous, filtered $V_{CO_2}$ data point, $V_{CO_2}'[n]$ is the new "filtered" value based on $V_{CO_2}[n]$ and obtained by use of the filter, and $\alpha$ is the filter coefficient. The filter coefficient, $\alpha$, has a range of 0 to 1.0. The greater the value of $\alpha$, the more profoundly the most recently calculated data point is filtered and, conversely, the lower $\alpha$ values cause the most recently calculated data points to be filtered to a lesser degree. When $\alpha$ is equal to zero, the most recently calculated data point is not filtered.

Due to anatomical and physiological differences between different patients, different patients have differing optimal filter coefficients, $\alpha$. In addition, as anatomical and physiological changes may occur in a patient over time, the optimum filter coefficient, $\alpha$, to be used in filtering the $V_{CO_2}$ or $CaCO_2$ values calculated from the patient's breathing may also vary over time. Any known optimization method or search algorithm may be employed to select optimal filter coefficient, $\alpha$.

Figure 5B:
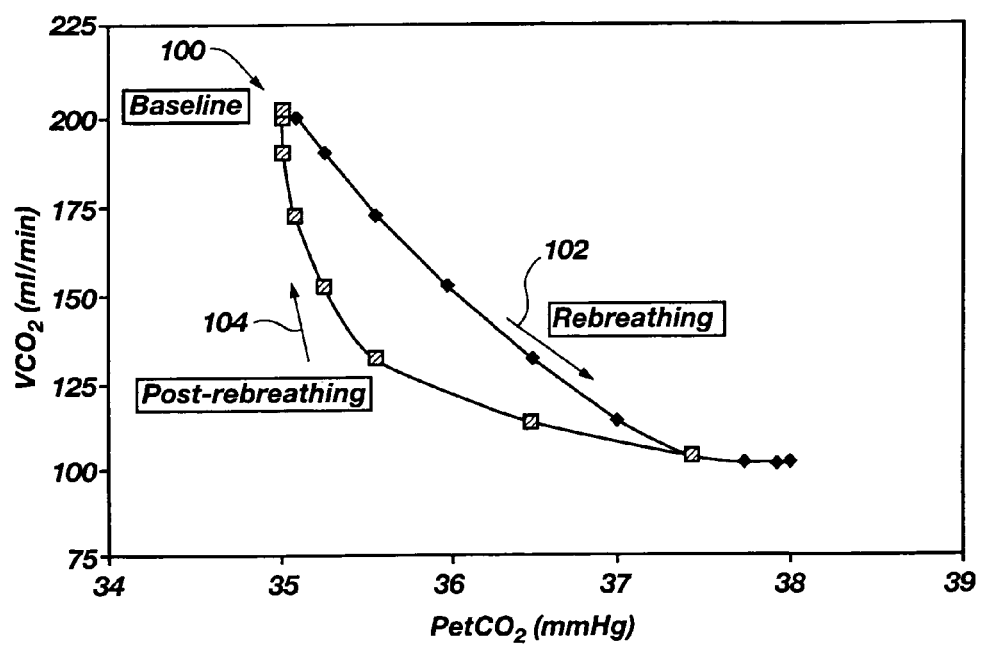
FIG. 5B is a two-dimensional line graph illustrating a plot of $V_{CO_2}$ on the y-axis and $CaCO_2$ on the x-axis following modification of the $V_{CO_2}$ and $CaCO_2$ data.
Figure 7:
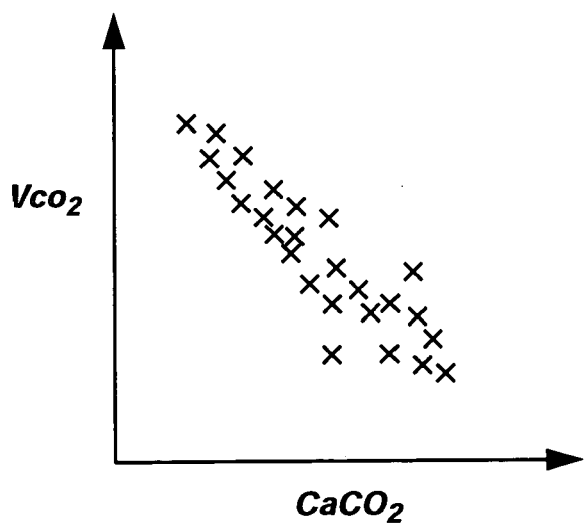
FIG. 7 is an exemplary two-dimensional plot depicting modified $V_{CO_2}$ and carbon dioxide content values from the same rebreathing cycle as that shown in FIG. 5A.

As an example of one way in which an optimal filter coefficient may be selected, $\alpha$ is first set to a default value (e.g., 0.85) and the calculated $V_{CO_2}$ or $CaCO_2$ values are filtered on the basis of the default filter coefficient, $\alpha$. The linear regression is then performed to obtain a best-fit line. If the correlation coefficient of the best-fit line calculated with the just-filtered data is less than the correlation coefficient of the immediately preceding best-fit line, which was calculated with unfiltered data or with a prior filter coefficient, then a predetermined α adjustment value (e.g., 0.01) is changed by multiplying the α adjustment value by −1 and by modifying the filter coefficient by adding the modified α adjustment value thereto. Otherwise, the filter coefficient, α, is modified by adding the unmodified α adjustment value thereto. The process of filtering the data based on a modified filter coefficient, obtaining a best-fit line for the data, comparing the correlation coefficient of the best-fit line to the correlation coefficient of the previous best-fit line, and adjusting the filter coefficient accordingly is then repeated a predetermined number of times (e.g., 50 times). The best-fit line with the greatest correlation coefficient, based on the unfiltered data and each set of filtered data, is selected to calculate the pulmonary capillary blood flow or cardiac output of the patient. When filtering is used, the $V_{CO_2}$-$CaCO_2$ plot preferably narrows, as depicted in FIGS. 5B and 7, to thereby increase the accuracy with which the location and orientation of a best-fit line can be established and, thus, to increase the accuracy of a pulmonary capillary blood flow or cardiac output determination based on the data.

Another example of a method for increasing the correlation coefficient between the $V_{CO_2}$ and $CaCO_2$ data and the best-fit line therefor, which is referred to herein as "clustering," includes the selection of data points that are grouped closely together. That is, the data points that are selected include those data points having a number of other data points within a predetermined range thereof. Data points that are not clustered are probably inaccurate or based on measurements taken during spurious breaths. As an accurate best-fit line through the data would likely be based on the clustered data, the data points that are not located in a cluster are not used in calculating the location and orientation of a best-fit line for the data.

Clustering of the data points may include normalization or transformation of the data such that ranges of the x-ordinate data (e.g., the $CaCO_2$ data) and the y-ordinate data (e.g., the $V_{CO_2}$ data) are substantially the same. Without such normalization, the data group (e.g., the $V_{CO_2}$ data or the $CaCO_2$ data) with the highest range would dominate; the other data group would be less significant.

An exemplary manner in which the data may be normalized includes use of the following normalization:

$$x = (x - \bar{x})/\sigma_x, \qquad (48)$$

where:

x is the raw value, $\bar{x}$ is the mean value of all x-axis (e.g., $CaCO_2$) data in the plot, and $\sigma_x$ is the standard deviation of all x-axis data in the plot. This normalization is applied to all x-axis values. A similar normalization scheme is applied to all of the y-axis values.

The normalized data may then be clustered by searching for a predetermined number (e.g., 5) of the closest data points (e.g., $V_{CO_2}$ or $CaCO_2$ data points) to each of the data points in a group. The differences between the analyzed data point and each of the predetermined number of closest data points are then added together and compared to a predetermined threshold. If the sum of the differences exceeds the predetermined threshold, the analyzed data point is discarded. Of course, the use of other clustering techniques to identify the most accurate data and to disregard probable inaccurate data are also within the scope of the present invention.

Once clustering has been performed, the inverse of the normalization is calculated, or the normalization is undone, to provide an accurate determination of pulmonary capillary blood flow or cardiac output. An example of the manner in which the inverse of the normalization may be calculated includes use of the following equation:

$$x = x\sigma_x + \bar{x}. \qquad (49)$$

This inverse of the normalization is applied to all of the clustered x-axis (e.g., $CaCO_2$) values. A similar inverse normalization scheme is applied to all of the clustered y-axis data.

Clustering is one of many known techniques for determining outliers. Other known techniques for determining outliers may also be used in the method of the present invention.

Alternatively, or in addition to disregarding probable inaccurate data points, in order to enhance the accuracy of the data, clustering can be used add synthetic data points. Synthetic data points may be added to increase the correlation coefficient of the best-fit line to the data points on which the best-fit line is based.

Figure 8A:
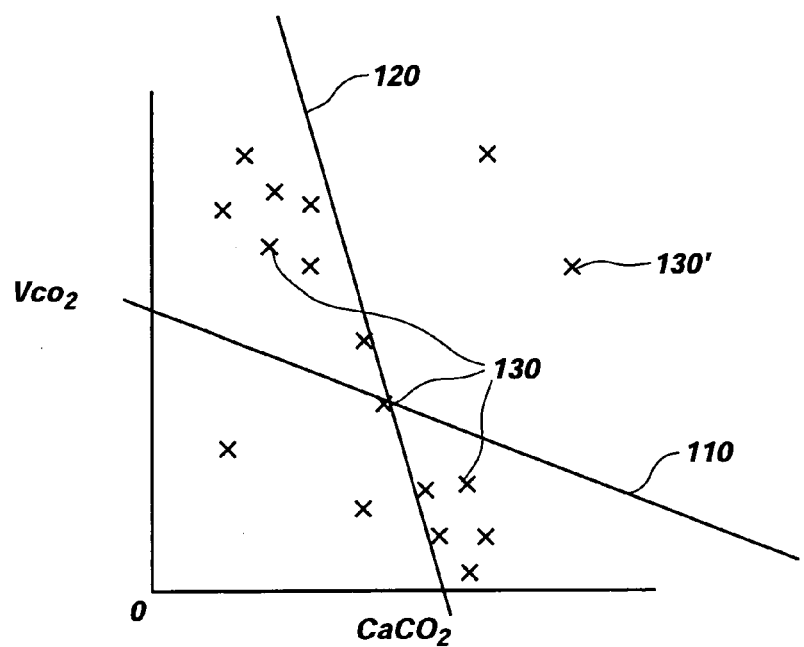
FIGS. 8A and 8B are two-dimensional plots illustrating an exemplary rebreathing technique and an accompanying method for modifying respiratory data to obtain an accurate best-fit line therethrough.
Figure 8B:
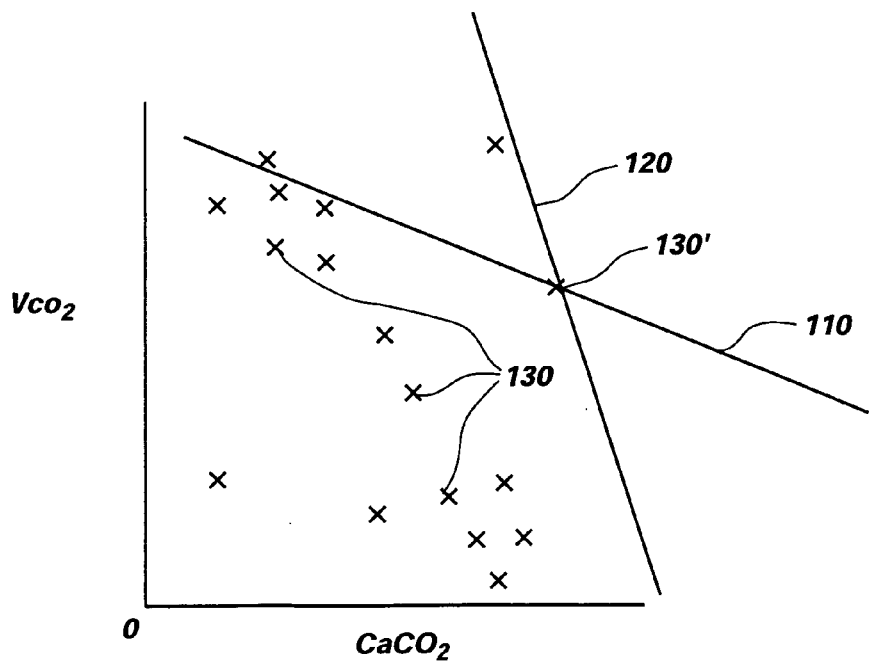

Another exemplary method for modifying data in the best-fit line method is depicted in FIGS. 8A and 8B. As with the filtering and clustering methods for modifying data, the method depicted in FIGS. 8A and 8B includes selection of data points that are most likely to facilitate an accurate determination of the location and orientation of a best-fit line and, thus, of the pulmonary capillary blood flow or cardiac output of a patient. This method for modifying data includes iteratively examining data points and the distribution of the remaining data points relative to the two lines representing the range of possible pulmonary capillary blood flow measurements.

As shown in FIGS. 8A and 8B, a line or the equation for a line 110 representing a minimum expected pulmonary capillary blood flow (i.e., $-m_{line} = PCBF_{min}$) and a line or the equation for a line 120 representing a maximum expected pulmonary capillary blood flow (i.e., $-m_{line\ 120} = PCBF_{max}$) are positioned to intersect at a data point 130. For example, when the x-ordinate is based on $CaCO_2$, line 110 may have a slope of −0.5, which represents a minimum expected pulmonary capillary blood flow of 0.5 L/min, and line 120 may have a slope of −20, which represents a maximum pulmonary capillary blood flow of 20 L/min. Of course, other pulmonary capillary blood flow values for lines 110 and 120 may also be used.

Next, the number of other data points 130 located between lines 110 and 120 is determined. If the number of data points 130 between lines 110 and 120 is equal to or exceeds a threshold number, the analyzed data point 130 is retained for a subsequent determination of the location and orientation of a best-fit line through the data. Otherwise, the analyzed data point 130 is discarded. The threshold number of data points that must be located between line 110 and line 120 for an analyzed data point to be retained may be a predetermined value or determined by other means. As an example, the threshold number may be set to the median number of data points that are located between line 110 and line 120 when each data point 130 of a set of data points 130 has been evaluated in accordance with the present embodiment of the method for modifying data. This process is repeated until each data point 130 in a set of data points 130 has been so evaluated. FIG. 8A depicts use of the data modification method on a data point 130 that will be retained, while FIG. 8B illustrates use of the present embodiment of the data modification method on another data point 130' that will not be retained.

FIGS. 5A and 5B and FIGS. 6 and 7 illustrate the effect of modifying data to increase the accuracy with which the location and orientation of a best-fit line through the data may be determined. FIG. 6 illustrates a typical $V_{CO_2}$ vs. $CaCO_2$ plot without such modification, where the plot appears as a loop. By way of contrast, FIG. 7 illustrates the closeness of the data when one or more of the embodiments of the method of the present invention are used to modify the data. FIGS. 5A and 5B illustrate plots of $V_{CO_2}$ and $PetCO_2$ data before and after modification, respectively. The increased closeness of the data points makes it possible to determine the orientation and location of a best-fit line therethrough with increased accuracy.

Once all of the data points have been examined, the location and orientation for the best-fit line through the remaining, clustered data are determined. Again, linear regression is preferably used to determine the location and orientation of the best-fit line. The negative slope (i.e., $-1 \times m$) of the best-fit line provides a pulmonary capillary blood flow measurement, which may then be used to determine cardiac output. A correlation coefficient can then be calculated, as previously disclosed herein, to indicate the quality of the data used to determine pulmonary capillary blood flow or cardiac output. The correlation coefficient or a quality measure based thereon may then be communicated to the user (e.g., a doctor, nurse, or respiratory technician) or used to weight the resulting pulmonary capillary blood flow or cardiac output value in an output, weighted average value.

One or a combination of the methods for modifying data may be performed on the measured or calculated data to increase the accuracy with which a best-fit line through the data or the pulmonary capillary blood flow or cardiac output of a patient can be determined.

As an example of the use of filtering and clustering together, the calculated $V_{CO_2}$ data are grouped together as the y-axis data of a two-dimensional line graph and the calculated $CaCO_2$ data points are grouped together as x-axis data points. The data points in at least one of the groups are filtered to determine a best-fit line for the data having an optimum correlation coefficient. The data are also clustered, either before or after filtering, to further improve the correlation coefficient of the best-fit line to the calculated $V_{CO_2}$ and $CaCO_2$ data. The remaining data is then used to determine (e.g., by linear regression) a best-fit line therefor, as well as a correlation coefficient for the best-fit line. The slope of the best-fit line is then calculated and used to determine pulmonary capillary blood flow or cardiac output. The correlation coefficient may also be used to indicate the reliability of the pulmonary capillary blood flow or cardiac output determination or to impart a specific weight to the pulmonary capillary blood flow or cardiac output determination in a weighted average thereof.

Once the location and orientation of an accurate best-fit line for the data has been determined, as disclosed previously herein, the pulmonary capillary blood flow of the patient can be calculated as the negative of the slope of the best-fit line.

In addition, the best-fit line can be used to estimate the $CvCO_2$ of the patient. When $V_{CO_2}$ eventually ceases during total rebreathing, the partial pressure of carbon dioxide measured at the mouth ($pCO_2$) of a patient may represent the $CvCO_2$ of the patient. When partial rebreathing techniques are used, the $V_{CO_2}$ of the patient is reduced to levels lower than baseline, but is not reduced to zero. By determining the best-fit line through data obtained by use of partial rebreathing techniques, the best-fit line can be extended to a point where $V_{CO_2}$ would be equal to zero or effectively zero and, thereby, used to determine the carbon dioxide content, or mixed venous carbon dioxide content ($CvCO_2$), of the patient's blood at that point. Equation (39), which is the equation for the best-fit line, can be rearranged in terms of carbon dioxide elimination as follows:

$$V_{CO_2} = m \times CaCO_2 + b. \tag{50}$$

When carbon dioxide elimination ceases, $V_{CO_2}$ is equal to zero and equation (50) becomes:

$$0 = m \times CvCO_2 + b, \tag{51}$$

which can be rearranged as follows:

$$CvCO_2 = -b/m. \tag{52}$$

Accordingly, the present invention also includes methods for substantially noninvasively determining $CvCO_2$ when partial rebreathing techniques are employed.

If the above-described processes are used to determine the pulmonary capillary blood flow of a patient, the intrapulmonary shunt flow of the patient or intrapulmonary shunt fraction of the cardiac output of the patient may also be determined, as known in the art. The cardiac output of the patient may then be determined from the pulmonary capillary blood flow and intrapulmonary shunt flow of the patient, as known in the art.

The relative short phases of differential Fick techniques incorporating teachings of the present invention, as well as the lack of a recovery or stabilization period, facilitate the calculation and, thus, reporting of noninvasive pulmonary capillary blood flow or cardiac output measurements with increased frequency over that possible with previously known differential Fick techniques. For example, when conventional partial rebreathing techniques are employed, pulmonary capillary blood flow and cardiac output values can only be updated as frequently as the cycle time for these methods, which is typically three minutes or longer. In contrast, when the differential Fick method of the present invention is embodied as a partial rebreathing process with rebreathing and nonrebreathing phases that last about thirty seconds, the pulmonary capillary blood flow and cardiac output of a patient can be updated following the completion of each phase, or about every thirty seconds.

While specific rebreathing processes are disclosed herein, the methods disclosed herein may also be used with other rebreathing processes, as well as with other differential Fick techniques for noninvasively measuring the pulmonary capillary blood flow or cardiac output of a patient.

The method of the present invention facilitates the measurement of pulmonary capillary blood flow or cardiac output on a more frequent basis. As a result, when methods of the present invention are employed, the pulmonary capillary blood flow or cardiac output of a patient may be better and more accurately tracked.

Although the foregoing description contains many specifics, these should not be construed as limiting the scope of the present invention, but merely as providing illustrations of some exemplary embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

What is claimed is:

1. A differential Fick technique, comprising:
inducing a change in effective ventilation of a subject for a first duration of time of approximately eighteen seconds to approximately forty-two seconds;
removing the change in effective ventilation for a second duration of time of approximately eighteen seconds to approximately forty-two seconds immediately following the first duration of time, wherein a transition between inducing the change and removing the change is gradual; and
obtaining measurements of at least one respiratory gas and of respiratory flow during both the first duration of time and the second duration of time.

2. The differential Fick technique of claim 1, further comprising repeating inducing immediately following the second duration of time.

3. The differential Fick technique of claim 2, wherein repeating is again effected for the first duration of time.

4. The differential Fick technique of claim 2, including obtaining measurements of the at least one respiratory gas and the respiratory flow during repeating.

5. The differential Fick technique of claim 1, wherein the firs duration of time of inducing and the second duration of time of removing are substantially the same.

6. The differential Fick technique of claim 5, wherein the first duration of time of inducing is at least about 30% of a combined duration of the first duration of time and the second duration of time.

7. The differential Fick technique of claim 5, wherein the second duration of time of removing is at least about 30% of a combined duration of the first duration of time and the second duration of time.

8. The differential Fick technique of claim 5, wherein inducing and removing are both effected for about 30 seconds.

9. The differential Fick technique of claim 5, wherein a combined duration of inducing and removing is at most about two minutes.

10. The differential Fick technique of claim 1, wherein inducing comprises causing the subject to rebreathe.

11. The differential Fick technique of claim 1, wherein obtaining measurements comprises obtaining measurements of carbon dioxide in respiration of the subject.

12. The differential Fick technique of claim 1, further comprising optimizing at least one of the first duration of time and the second duration of time.

13. The differential Fick technique of claim 1, further comprising optimizing the first and second durations of time.

14. The differential Fick technique of claim 13, wherein optimizing is based on ventilation of the subject.

15. The differential Fick technique of claim 14, wherein optimizing is further based on at least one of a pulmonary capillary blood flow and a cardiac output of the subject.

16. A method for noninvasively determining at least one of a pulmonary capillary blood flow and a cardiac output of a subject, comprising:
inducing a change in effective ventilation of the subject for a first period of time;
removing the change in effective ventilation of the subject for a second period of time, which is substantially the same as the first period of time, immediately following inducing; and
repeating inducing immediately following the second period of time.

17. The method of claim 16, including obtaining measurements of at least one respiratory gas and respiratory flow during inducing and removing.

18. The method of claim 17, wherein obtaining measurements comprises obtaining a measurement of at least carbon dioxide in respiration of the subject.

19. The method of claim 16, wherein the first period of time of inducing and the second period of time of removing are substantially the same.

20. The method of claim 16, wherein inducing comprises rebreathing.

21. The method of claim 16, further comprising optimizing at least one of the first period of time and the second period of time.

22. The method of claim 16, wherein a transition between inducing the change and removing the change is gradual.

23. The method of claim 16, further comprising optimizing the first and second periods of time.

24. The method of claim 23, wherein optimizing is based on effective ventilation of the subject.

25. The method of claim 24, wherein optimizing is further based on at least one of a pulmonary capillary blood flow and a cardiac output of the subject.

26. A method for noninvasively determining at least one of a pulmonary capillary blood flow and a cardiac output of a subject, comprising:
evaluating respiration of the subject during a first phase in which a change in effective ventilation of the subject is induced for a first period of time; and
evaluating respiration of the subject following removal of the change in effective ventilation of the subject; the removal being effected for a second period of time immediately following the first period of time, the first and second periods of time each lasting for approximately eighteen seconds to approximately forty-two seconds;
repeating the first phase immediately following the second period of time and evaluating respiration of the subject during repeating.

27. The method of claim 26, wherein evaluating respiration of the subject during the first phase and evaluating respiration of the subject following removal of the change in effective ventilation are effected for substantially the same duration of time.

28. The method of claim 26, wherein each of evaluating respiration during the first phase and evaluating respiration following removal of the change comprises measuring at least one respiratory gas and respiratory flow of the subject.

29. The method of claim 28, wherein measuring at least one respiratory gas comprises measuring at least respiratory carbon dioxide of the subject.

30. The method of claim 26, wherein evaluating respiration of the subject during the first phase comprises evaluating respiration of the subject during rebreathing.

31. The method of claim 26, further comprising optimizing at least one of the first period of time and the second period of time.

32. The method of claim 26, wherein a transition between the first phase and the removal is gradual.

33. The method of claim 26, further comprising optimizing the first and second periods of time.

34. The method of claim 33, wherein optimizing is based on ventilation of the subject.

35. The method of claim 34, wherein optimizing is further based on at least one of a pulmonary capillary blood flow and a cardiac output of the subject.

36. A method for noninvasively estimating at least one of a pulmonary capillary blood flow and a cardiac output of a subject, comprising:
evaluating respiration of the subject during a first ventilation state having a duration of approximately eighteen seconds to approximately forty-two seconds;
evaluating respiration of the subject during a second ventilation state having a duration of approximately eighteen seconds to approximately forty-two seconds; and
optimizing a duration of at least one of the first ventilation state and the second ventilation state.

37. The method of claim 36, wherein evaluating respiration of the subject during the first ventilation state is effected for about 30 seconds.

38. The method of claim 36, wherein evaluating respiration of the subject during the second ventilation state is effected for about 30 seconds.

39. The method of claim 36, wherein evaluating respiration of the subject during the first ventilation state is effected for a duration of at least about 30% of a combined duration of evaluating respiration of the subject during both the first ventilation state and the second ventilation state.

40. The method of claim 36, wherein evaluating respiration of the subject during the second ventilation state is effected for a duration of at least about 30% of a combined duration of evaluating respiration of the subject during both the first ventilation state and the second ventilation state.

41. The method of claim 36, wherein evaluating respiration of the subject during the first ventilation state and the evaluating respiration of the subject during the second ventilation state are effected for a combined duration of at most about two minutes.

42. The method of claim 36, wherein evaluating respiration of the subject during the first ventilation state comprises evaluating respiration of the subject during rebreathing.

43. The method of claim 36, wherein evaluating respiration of the subject during the first ventilation state comprises employing a best-fit line method of rebreathing.

44. The method of claim 36, wherein evaluating respiration of the subject during the second ventilation state comprises evaluating respiration of the subject while the subject is breathing air.

45. The method of claim 36, wherein evaluating respiration of the subject during the second ventilation state comprises evaluating respiration of the subject while the subject is breathing gas or a gas mixture comprising at least a concentration of oxygen present in air.

46. The method of claim 36, wherein evaluating respiration of the subject during the first ventilation state is conducted immediately before evaluating respiration of the subject during the second ventilation state.

47. The method of claim 36, wherein evaluating respiration of the subject during the second ventilation state is effected before calculating the pulmonary capillary blood flow or cardiac output of the subject.

48. The method of claim 36, wherein a transition between the first and second ventilation states is gradual.

49. The method of claim 36, wherein optimizing includes optimizing durations of the first and second ventilation states.

50. The method of claim 49, wherein optimizing is based on ventilation of the subject.

51. The method of claim 50, wherein optimizing is further based on at least one of a pulmonary capillary blood flow and a cardiac output of the subject.

52. The method of claim 46, further comprising repeating evaluating respiration of the subject during another first ventilation state immediately following evaluating respiration of the subject during the second ventilation state.

53. A method for noninvasively estimating at least one of a pulmonary capillary blood flow and a cardiac output of a subject, comprising:
evaluating respiration of the subject during a first ventilation state comprising rebreathing;
evaluating respiration of the subject during a second ventilation state immediately following the first ventilation state; and
evaluating respiration of the subject during another first ventilation state immediately following the second ventilation state, each of the first ventilation state, the second ventilation state, and the another first ventilation state having a duration of approximately eighteen seconds to approximately forty-two seconds.

54. The method of claim 53, wherein evaluating respiration of the subject during the first ventilation state and the evaluating respiration of the subject during the second ventilation state are effected for substantially a same duration.

55. The method of claim 53, wherein evaluating respiration of the subject during the first ventilation state is effected for about 30 seconds.

56. The method of claim 53, wherein evaluating respiration of the subject during the second ventilation state is effected for about 30 seconds.

57. The method of claim 53, wherein evaluating respiration of the subject during the another first ventilation state is effected for about 30 seconds.

58. The method of claim 53, wherein evaluating respiration of the subject during the first ventilation state is effected for at least about 30% of a combined duration of the evaluating respiration of the subject during the first ventilation state and evaluating respiration of the subject during the second ventilation state.

59. The method of claim 53, wherein evaluating respiration of the subject during the second ventilation state is effected for at least about 30% of a combined duration of the evaluating respiration of the subject during the first ventilation state and the evaluating respiration of the subject during the second ventilation state.

60. The method of claim 53, wherein evaluating respiration of the subject during the first ventilation state and the evaluating respiration of the subject during the second ventilation state are effected for a combined duration of at most about 2 minutes.

61. The method of claim 54, wherein evaluating respiration of the subject during the another first ventilation state is effected for substantially the same duration.

62. The method of claim 53, wherein evaluating respiration of the subject during the first ventilation state comprises employing a best-fit line method of rebreathing.

63. The method of claim 53, wherein evaluating respiration of the subject during the second ventilation state comprises evaluating respiration of the subject while the subject is breathing air.

64. The method of claim 53, wherein evaluating respiration of the subject during the second ventilation state comprises evaluating respiration of the subject while the subject is breathing gas or a gas mixture comprising at least a concentration of oxygen present in air.

65. The method of claim 53, further comprising optimizing a duration of at least one of the first ventilation state and the second ventilation state.

66. The method of claim 53, wherein a transition between the second ventilation state and at least one of the first ventilation state and the another first ventilation state is gradual.

67. The method of claim 53, further comprising optimizing durations of the first and second ventilation states.

68. The method of claim 67, wherein optimizing is based on ventilation of the subject.

69. The method of claim 68, wherein optimizing is further based on at least one of a pulmonary capillary blood flow and a cardiac output of the subject.

70. A differential Fick technique, consisting essentially of:
a first phase in which a change in the effective ventilation of a subject is induced; and
a second phase following the first phase and during which a change in the effective ventilation of the subject is not present, the first phase and the second phase having substantially the same duration,
wherein the first and second phases are repeated in immediate sequence with one another.

71. The differential Fick technique of claim 70, wherein durations of the first and second phases are optimized.

72. The differential Fick technique of claim 70, wherein the first and second phases each have a duration of about 30 seconds.

73. The differential Fick technique of claim 70, wherein a duration of the first phase is at least about 30% of a combined duration of the first and second phases.

74. The differential Fick technique of claim 70, wherein a duration of the second phase is at least about 30% of a combined duration of the first and second phases.

75. The differential Fick technique of claim 71, wherein optimization of the durations of the first and second phases is based on ventilation of the subject.

76. The differential Fick technique of claim 70, wherein a combined duration of the first and second phases is at most about two minutes.

77. The differential Fick technique of claim 70, wherein the first phase comprises a rebreathing phase and the second phase comprises a nonrebreathing phase.

78. The differential Fick technique of claim 70, further comprising optimizing a duration of at least one of the first and second phases.

79. The differential Fick technique of claim 70, wherein the second phase occurs before the first phase.

80. The differential Fick technique of claim 70, wherein a transition between the first phase as the second phase is gradual.

81. The differential Fick technique of claim 75, wherein the optimization is further based on at least one of a pulmonary capillary blood flow and a cardiac output of the subject.

* * * * *